United States Patent [19]
Grosveld et al.

[11] Patent Number: 6,110,666
[45] Date of Patent: Aug. 29, 2000

[54] LOCUS CONTROL SUBREGIONS CONFERRING INTEGRATION-SITE INDEPENDENT TRANSGENE EXPRESSION ABSTRACT OF THE DISCLOSURE

[75] Inventors: Franklin Gerardus Grosveld, Rotterdam, Netherlands; James Ellis, Toronto, Canada; Dimitris Kioussis, London, United Kingdom

[73] Assignee: Medical Research Council, London, United Kingdom

[21] Appl. No.: 08/488,145

[22] Filed: Jun. 7, 1995

Related U.S. Application Data

[63] Continuation-in-part of application No. 08/314,657, Sep. 29, 1994, abandoned.

[30] Foreign Application Priority Data

Jun. 9, 1994 [GB] United Kingdom .................... 9411618

[51] Int. Cl.$^7$ ............................. C12Q 1/68; C12N 15/63; C12N 15/64; C12N 15/90
[52] U.S. Cl. ......................... 435/6; 435/172.1; 435/172.3
[58] Field of Search ......................... 435/6, 172.1, 172.3; 800/2

[56] References Cited

FOREIGN PATENT DOCUMENTS

WO 91/05041  4/1991  WIPO.

OTHER PUBLICATIONS

Fraser et al., "Each hypersenstive site of the human β–globin locus control region confers a different developmental pattern of expression on the globin genes," Genes & Dev. 7:106–113 (1993).

Ellis et al., "Synthetic human β–globin 5'HS2 constructs function as locus control regions only in multicopy transgene concatamers," The EMBO Journal 12:127–134 (1993).

Philipsen et al., "The β–globin dominant control region: hypersensitive site 2," The EMBO Journal 9:2159–2167 (1990).

Fraser et al., "DNaseI hypersensitive sites 1, 2 and 3 of the human β–globin dominant control region direct position–independent expression," Nucleic Acids Research 18:3503–3508 (1990).

Philipsen et al., "The minimal requirements for activity in transgenic mice of hypersensitive site 3 of the β–globin locus control," The EMBO Journal 12:1077–1085 (1993).

Miller et al., Single–Copy Transduction and Expression of Human γ–Globin in K562 Erythroleukemia Cells Using Recombinant Adeno–Associated Virus Vectors: . . . Blood 82:1900–1906 (1993).

Collins et al., "Definition of the minimal requirements within the human β–globin gene and the dominant control region for high level expression," The EMBO Journal 9:233–240 (1990).

Lang et al., "The structure of the human CD2 gene and its expression in transgenicm mice," The EMBO Journal 7:1675–1682 (1988).

Grosveld et al., "Position–Independent, High–Level Expression of the Human β–Glogin Gene in Transgenic Mice," Cell 51:975–985 (1987).

Reitman et al., "An Enhancer/Locus Control Region Is Not Sufficient To Open Chromatin", Molecular and Cellular Biology, vol. 13, No. 7, pp. 3990–3998, (Jul., 1993).

Pawlik et al., "Autonomous, Erythroid–Specific DNase I Hypersensitive Site Formed by Human β–Globin Locus Control Region (LCR) 5' HS 2 in Transgenic Mice", Developmental Biology, vol. 169, pp. 728–732, (1995).

Thompson et al., "Scaffold Attachment Regions Stimulate HSP70.1 Expression in Mouse Preimplantation Embryos but Not in Differentiated Tissues", Molecular and Cellular Biology, vol. 14, No. 7, pp. 4694–4703, (Jul. 1994).

Lang et al., "Deletion analysis of the human CD2 gene locus control region in transgenic mice", Nucleic Acids Research, vol. 19, No. 21, pp. 5851–5856, (1991).

Dlaz et al. Immunity 1 207–217, 1994.

Palmiter et al. Mol. Cell. Biol. 13(9) 5266–5275, 1993.

Theisen et al EMBO J 5(4) 719–724, 1986.

Greaves et al Cell 56 979–986, 1989.

Talbot et al. Nature 338 352–355, 1989.

Grosveld et al. Cell 51 975–985, 1987.

Collis et al. EMBO J 9(1) 223–240, 1990.

*Primary Examiner*—Nancy Degen
*Attorney, Agent, or Firm*—Kathleen M. Williams Ph.D.; Banner & Witcoff, Ltd.

[57] ABSTRACT

The invention encompasses a locus control subregion that possesses chromatin opening domain activity, the activity conferring reproducible activation of tissue-specific expression on a linked transgene to a non-physiological level when the transgene is integrated in single copy in the genome of a host cell.

3 Claims, 8 Drawing Sheets

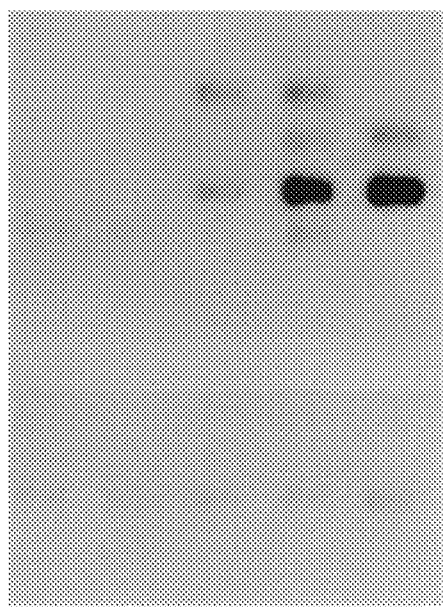
FIG. 1C
FIG. 1D
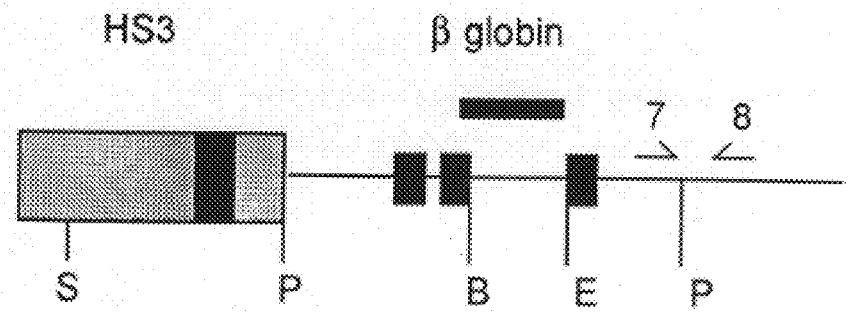
FIG. 4
| $F_0$ | $F_1$ | Lines |
|---|---|---|
| 6/71 | 60/124 | 6 |

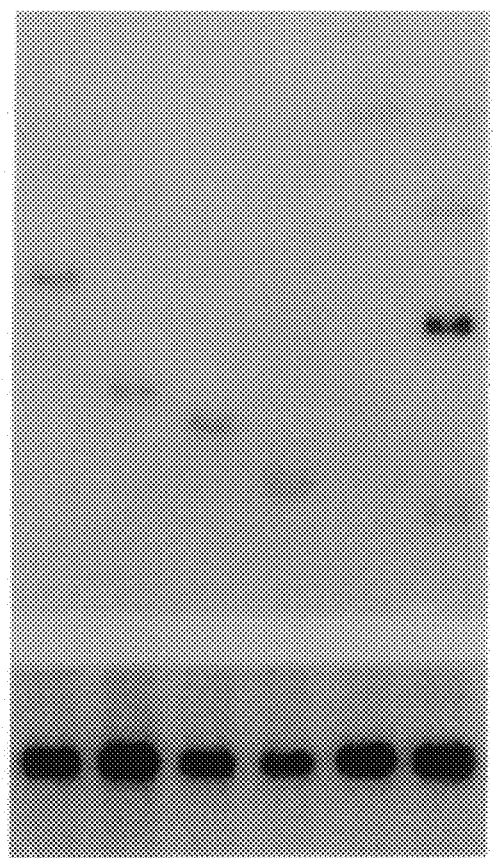
FIG. 5A
FIG. 5B Thy-1—
FIG. 8
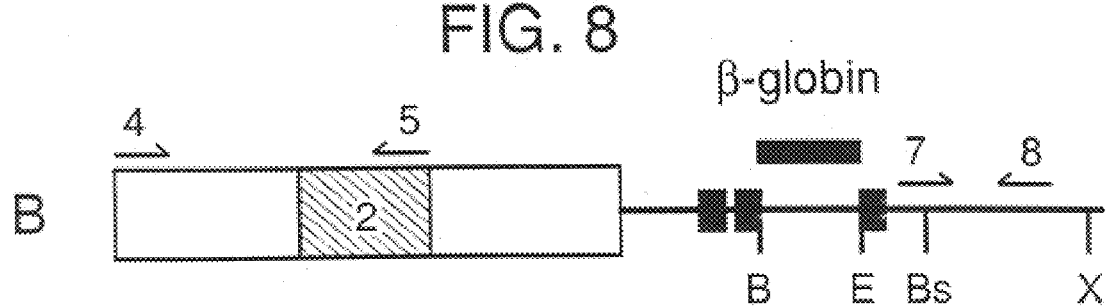
| $F_0$ | $F_1$ | LINES |
|---|---|---|
| 8/55 | 33/119 | 6 |

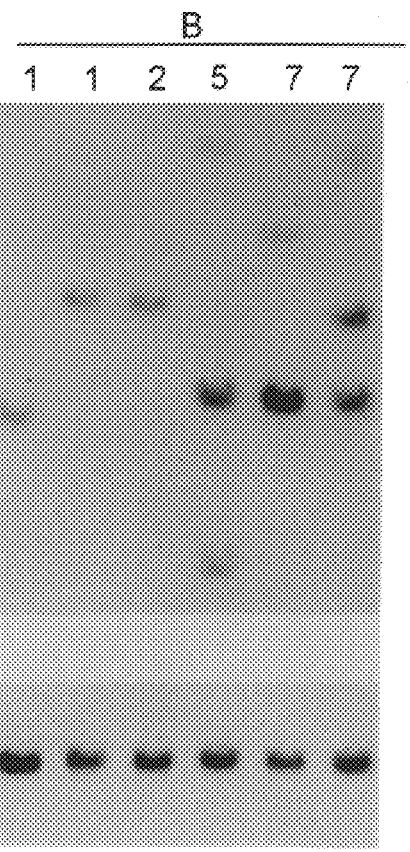
FIG. 9A
FIG. 9B
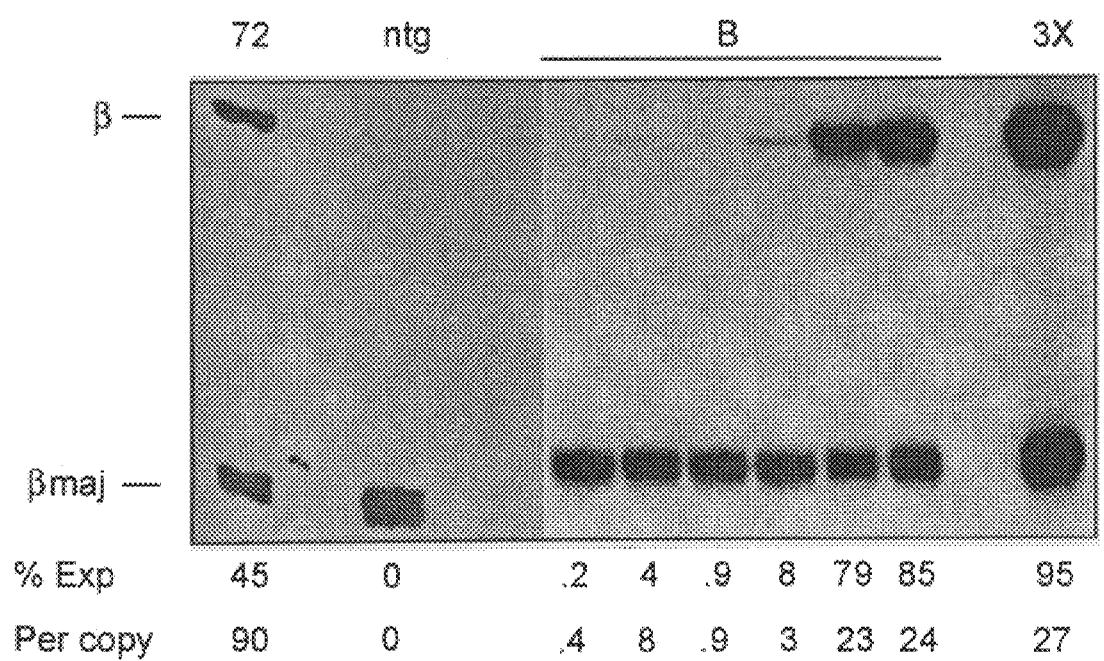
FIG. 10

LOCUS CONTROL SUBREGIONS CONFERRING INTEGRATION-SITE INDEPENDENT TRANSGENE EXPRESSION

ABSTRACT OF THE DISCLOSURE

This application is a continuation-in-part application of U.S. Ser. No. 08/314,657, filed Sep. 29, 1994 now abandoned.

FIELD OF THE INVENTION

The invention relates to the expression of heterologous genes in eukaryotic host cells and transgenic animals.

BACKGROUND OF THE INVENTION

Locus Control Regions (LCRs) (Grosveld et al., Cell 51:975–985, 1987), also known as Dominant Activator Sequences, Locus Activating Regions or Dominant Control Regions, are responsible for conferring tissue specific, integration-site independent, copy number dependent expression on transgenes integrated into chromatin in host cells. The discovery and characterization of LCRs are described in co-pending U.S. Ser. No. 07/920,536, filed Jul. 28, 1992, assigned to the same assignee, the complete disclosure of which is hereby incorporated by reference. First discovered in the human globin gene system, which was prone to strong position effects when integrated into the chromatin of transgenic mice or mouse erythroleukaemia (MEL) cells (Magram et al., Nature 315:338–340, 1985; Townes et al., EMBO J. 4:1715–1723, 1985; Kollias et al., Cell 46:89–94, 1986; Antoniou et al., EMBO J. 7:377–384, 1988), LCRs have the ability to overcome such position effects when linked directly to transgenes (Grosveld et al., supra). Numerous LCRs have been defined in the art, including but not limited to the β-globin and CD2 LCRs (European Patent Application 0 332 667), the macrophage-specific lysozyme LCR (Bonifer et al., 1985), and a class II MHC LCR (Carson et al., Nucleic Acids Res. 21, 9:2065–2072, 1993).

The complete β-globin LCR comprises four DNase I hypersensitive sites (HS) on a 20 kbp fragment that is too large to be incorporated into retrovirus or adeno-associated virus (AAV) vectors designed for integration into the mammalian genome. Individual hypersensitive sites, in particular the 5'HS2 associated element, have been studied for the ability to regulate transduced globin genes (Novak et al., Proc. Natl. Acad. Sci. USA 87:3386–3390, 1990; Chang et al., Proc. Natl. Acad. Sci. USA 89:3107–3110, 1992; Miller et al., Blood 82:1900–1906, 1993). However, it has proven to be difficult to obtain stable high-titer viruses bearing these sequences.

When referring to the DNase I hypersensitive sites of the β-globin LCR, care must be taken over the nomenclature used. Originally, the hypersensitive sites were numbered consecutively 1 to 4 working upstream from the globin genes by Tuan et al., (Proc. Natl Acad. Sci. USA 86:2554–2558, 1985) and downstream towards the gene by Grosveld et al. (supra). In 1990, agreement was reached to use the nomenclature in which 5'HS1 is closest to the globin genes and 5'HS4 is most distant from the genes. The GenBank numbering for HS2, HS3 and HS4 is GenBank 958–1714, GenBank 4248–5197, and GenBank 8486–8860, respectively. A number of publications dating back from around or before 1990 use the inverse nomenclature.

Previous work demonstrated that each hypersensitive site of the human β-globin locus control region confers a different developmental pattern of expression on the globin genes (Fraser et al., 1993, Genes & Development 7:106–113). HS3 was shown to be most active during the embryonic period, whereas HS4 showed the highest activity during the adult stage. Each of HS1 and HS2 drive equivalent levels, albeit low and high levels, respectively, of γ or β transgene expression throughout development.

Previous work demonstrated that the 5' HS2 core region, i.e., a 215 bp fragment containing four putative transcription factor binding sites, functions in a concatemer of at least two copies but not when present as a single copy in transgenic mice to confer position independent expression of a linked transgene (Ellis et al., Eur. Mol. Biol. J. 12:127–134, 1993). Thus, two or more 5'HS2 cores may interact and cooperate with each other to open chromatin and enhance transcription, however, a single 5'HS2 core fails to activate expression from a linked β-globin gene in single-copy founder transgenic mice. This failure of the single copy HS2/transgene construct to activate transgene transcription was demonstrated unequivocally using fully transgenic $F_1$ offspring. No such data exists in the prior art for the HS3 or HS4 β-globin LCR subregions.

HS3 and HS4 have only been tested in founder ($F_0$) animal tissue, that is, using embryo tissue that has been grown from injected eggs, which tissue can carry different copy numbers of a transgene in different cells. (Philipsen et al., 1993, EMBO J. 12:1077–1085; Pruzina et al., 1991, Nucleic Acids Res. 19;1413–1419).

Studies using founder animal tissue are highly inconclusive with respect to transgene copy number because copy number cannot be determined definitively. Because a transgene integrates into the injected egg after the single cell stage, different tissues almost always contain different copy numbers (or no copies) of a transgene. Therefore, reliable data as to expression of an HS3/or HS4/transgene construct in single copy cannot be obtained using founder animals. There is no indication in founder animals of the extent to which the transgene has integrated into the animal's somatic tissues. For instance, a nominal copy number of two could indicate the presence of two copies of the transgene in each cell, or four copies in half of the cells, or eight copies in one quarter of the cells, and so on. In addition, because of the minute amount of embryo tissue available, e.g., fetal liver tissue, copy number analysis in founder animals is performed on tissues other than that used for analysis of the expression level of the transgene. However, true copy number can be determined reliably in $F_1$ generation animals in which the transgene has been passed through the germ line by breeding of the founder animal. $F_1$ transgenic animals contain an equal number of copies of the transgene in each cell.

When experiments are conducted on single-copy transgenic animals, it is found that many of the LCR fragments previously believed to confer LCR activity are incapable of satisfying the functional requirement of an LCR, namely the conferring of integration-site independent expression on a transgene, when present in a single copy. Clearly, such DNA elements are inappropriate for protocols where the use of single copy gene is desirable, essential or inevitable, as in the case of many virus-based delivery systems.

Previously, it has been found that the full activity of an LCR appears to be obtainable only with complete LCR sequences. Thus, in the β-globin LCR, only a construct containing the DNA sequences surrounding all four of the DNase I hypersensitive sites 1 to 4 confers tissue-specific, integration site independent, copy number dependent expression of a transgene at levels reflecting the level of expression of an equivalent endogenous gene.

It is an object of the invention to provide for reproducible integration-site independent expression of a transgene in a mammal, particularly a human, when the transgene is integrated in single copy in the mammalian genome.

Another object of the invention is to identify a subfragment of an LCR that reproducibly confers the chromatin opening activity of the LCR when present in single copy.

Yet another object of the invention is to provide an LCR subregion which, when operatively associated with a transgene and integrated in single copy in a host cell genome, reproducibly confers integration-site independent, tissue-specific expression on the transgene.

Another object of the invention is to provide for reproducible, tissue-specific, integration-site independent expression of a single copy transgene using gene transfer techniques that are limited with respect to the amount of DNA that is transferred to a host genome.

SUMMARY OF THE INVENTION

The invention is based on the discovery that the chromatin opening function of a Locus Control Region (LCR) is separable from other functions of an LCR, and may be carried on a portable subfragment of the LCR. The present invention is directed to gene therapy through delivery of a recombinant DNA vector containing a chromatin opening domain and a functional (expressible) gene to the cells of a patient, and expression of the gene in a position independent manner.

The present invention accordingly provides a recombinant DNA vector comprising an LCR subregion comprising a chromatin opening domain operably linked to an expressible gene, and a carrier for introducing the vector into a host cell via transmembrane delivery.

Preferably, the transmembrane delivery carrier will include one of a protein carrier as for cell-cell fusion, an antibody carrier, a liposomal carrier and viral carriers. More preferably, the carrier for vector delivery includes carriers which deliver the vector via the process known as receptor-mediated endocytosis, i.e., the use of a ligand capable of binding to a membrane receptor, the complex of which is taken into the cell via membrane invagination.

A "chromatin opening domain" is characterized in that, when it is operably linked to a gene and integrated in single copy into the genome of a host cell, it reproducibly actuates tissue-specific expression of the gene to a non-physiological level, i.e., a level that is below the level of expression of a transgene that is operably linked to an equivalent fully functional LCR, independent of the site of integration of the gene in the genome.

As used herein, "chromatin opening domain" refers to a region of DNA that is defined in terms of both its structure and function. Structurally, the region is defined in that it comprises a region of an LCR that encompasses at least one DNase I hypersensitive site when the region is in its native (i.e., naturally occurring) context in the chromosome; functionally, it is defined in that it possesses the property of actuating transcription of a linked gene independent of the integration site of the gene in a host cell genome. "Actuating transcription" refers to the ability of the domain to allow for activation of transcription of the linked gene. This process of actuating transcription is believed to involve the ability of the chromatin opening domain to render the region of chromatin encompassing the linked gene (or at least its promoter) accessible to transcription factors. An "expressible" gene refers to a gene and genetic control elements necessary for expression of the gene in a host cell.

As will be understood by a person skilled in the art, a locus control region (LCR) is a region of DNA that confers copy number dependent and integration site independent expression of a linked gene (i.e., a gene with which it is associated).

It has been observed that a fully-functional LCR directs expression of a transgene to a physiological level, i.e., a level equivalent to that observed for an equivalent endogenous gene. In contrast, an LCR subregion comprising a chromatin opening domain that is the subject of this invention does not achieve the full activity of an LCR but activates transcription at a non-physiological, i.e., lower level. Preferably, the lower level is less than or equal to about 80% of a physiological level; more preferably, less than about 60%; and most preferably, less than about 45%. By "physiological level of a gene product" is meant a level of gene function at which a cell population or patient exhibits the normal physiological effects made by the presence of normal amounts of the encoded protein. Insufficient amounts of a gene product will result in deleterious or unwanted clinical symptoms, e.g., as are associated with a disease.

Preferably, a domain of the invention is associated with, i.e., encompasses, a DNase I hypersensitive site in the genome of a cell. It is believed that the majority of LCRs will be found to be associated with DNase I hypersensitive sites in natural cell chromatin and moreover it appears that discrete elements of the LCR are marked by single hypersensitive sites within a cluster of sites which is associated with the presence of the complete LCR.

A fully functional or complete LCR will, of course, include a chromatin opening domain. The ability to convert chromatin to an open conformation is a key feature of an LCR, particularly for those uses of the invention involving expression of single-copy transgenes. This function has been discovered to be separable from other functions of the LCR which act to confer physiological level expression. The chromatin opening DNA element of the invention is a region of DNA that transforms a closed chromatin structure into an open chromatin structure.

A chromatin opening domain of the invention is in its native context part of a fully functional LCR.

A chromatin opening domain of the invention also preferably restores the DNase I hypersensitivity found in the subregion in its native chromatin context to the subregion when integrated in a host cell genome.

LCRs display tissue specificity in their behavior, and the chromatin opening domains of the invention possess equally tissue-specific characteristics. Therefore, the appropriate domain will be selected according to its tissue-specific characteristics, such that it will function to actuate transgene expression only in a desired tissue. For example, the β-globin or macrophage-specific lysozyme LCRs are specific for a particular hematopoietic cell lineage. It will be apparent to those skilled in the art that appropriate LCR subregions may be selected for individual applications, as required.

One of skill in the art would be able to determine if a chromatin opening domain exists in a region of DNA by cloning a region of DNA that is suspected of containing such a domain, linking the cloned region to a reporter gene to generate a construct, introducing the construct into a host cell, preferably of a mammal, and measuring RNA encoded by the linked gene (or a portion thereof) relative to the amount of RNA encoded by an endogenous gene that is under the control of an equivalent endogenous locus control region in the host cell. The cloned region of DNA will be determined to contain a chromatin opening domain if actuation of transcription of the linked gene is reproducibly obtained among host cell genomes containing single copy chromatin opening domain/transgene constructs. Typically, 3–5 single copy host cell genomes (e.g., transgenic animals) will be tested for transgene transcription in order to ascertain reproducible actuation of transcription. Moreover, the linked gene will express an amount of RNA that is less than about 80% (i.e., in the range of 1–80%), preferably less than about 60% or 45% of the amount of RNA that is expressed by a single copy of the endogenous gene.

The invention thus also encompasses testing a region of a tissue specific locus for chromatin opening domain activity, such activity being defined herein as conferring tissue specificity of the locus from which the domain is derived and conferring position independent gene expression, the activity being conferred by a region of DNA that is smaller than the region identified as a locus control region (i.e., including an associated enhancer), and the level of transgene expression conferred being less than that conferred by the corresponding fully functional LCR. The testing construct includes a reporter gene, such as the β-galactosidase reporter gene driven by the mouse heat shock promoter 68 (hsp 68). Other reporter genes are also contemplated according to this aspect of the invention, including but not limited to the luciferase gene.

In one embodiment of this aspect of the invention, the β-galactosidase reporter gene and the mouse heat shock promoter 68 are operationally associated with the β-globin HS3 COD. Thus, the construct is introduced into cells of a lineage for which the tested COD is tissue specific, e.g., blood cells for the β-globin HS3 COD, and expression of the reporter transgene is detected and optionally quantified in that tissue.

The domains of the invention are typically much smaller than the fully-functional LCR. For example, the fully-functional β-globin LCR is 20 kb in length, while the smallest domain identified which has the ability to confer an open chromatin conformation is 1.9 kb in length. This reduction in size is advantageous in that it allows for packaging of LCR-active constructs into available viral delivery systems. Many viral delivery systems for the delivery of genes encoding therapeutic products involve integration of transferred DNA in single copy in host cells. Moreover, use of single copy integrants reduces the risk of possible adverse effects on the host cell genome by ensuring that the number of DNA recombination events is kept to the absolute minimum. Packaging into alternative, non-viral delivery systems and vectors is also facilitated.

The invention thus enables constructs having LCR activity which are considerably smaller than was previously possible using the entire LCR. A construct according to the invention is active when integrated in single copy number, thus providing reproducible long-term (stable) expression of a transgene.

The invention further provides domains according to the invention for use in medicine. In particular, the domains of the invention are indicated for use in the manufacture of medicaments. For example, products such as human growth hormone or human factors VIII or IX may be made in a transgenic animal using a construct of the invention.

Chromatin opening domains according to the invention may be found in association with a variety of LCR sequences. The LCR sequences are preferably of mammalian origin, but other vertebrate sequences, such as avian LCR sequences, are known.

One detailed embodiment of the invention provides a chromatin opening domain that is associated with one of the four DNase I hypersensitive sites of the human β-globin LCR in native chromatin. It has been discovered that the DNA sequence surrounding 5'HS3 in the human β-globin LCR is responsible for reproducibly directing actuation of transcription of a linked transgene when the construct is present in single copy in transgenic mice, independent of the site of integration of the construct in the mouse genome.

Preferably, the 5'HS3 construct comprises the 1.9 kb DNA sequence between the Hind III sites 14.3 to 16.2 kb upstream of the ε-globin gene.

After having identified a DNA sequence responsible for conferring chromatin activation, as taught herein, it will be apparent to one skilled in the art that one can combine such a sequence with a chosen enhancer element to increase the expression level of a transgene. For example, use of a strong heterologous enhancer with a domain of the invention may lead to physiological-level expression of the transgene in the desired tissue type, independently of the site of integration of transgene in host cell chromatin. Strong enhancers are well-known in the art and include, e.g., the β-globin HS2 or HS4 enhancers, the α-globin enhancer, and certain viral enhancers known in the art. Use of a regulatable enhancer, e.g., hormone-inducible enhancers such as steroid, especially glucocorticoid-induced enhancers, or viral enhancers, can provide further control over the expression of the transgene. Other suitable enhancer constructs are well known in the art and may be selected for their known properties.

A construct according to the invention may include a chromatin opening domain in combination with a heterologous enhancer. The heterologous COD/enhancer combination allows one of skill in the art to choose a combination which will confer a desired level of transgene expression, i.e., that is not achievable using a homologous COD/enhancer combination. The heterologous COD/enhancer combination will achieve a level of transgene expression that is either less than or greater than the level of transgene expression achieved using a homologous COD/enhancer combination. As used herein, "greater than" or "less than" means at least 10% or preferably 20–25% greater than or less than the level of expression of a homologous COD/enhancer combination.

Other heterologous enhancers useful according to this aspect of the invention include but are not limited to the human Cytomegalovirus (CMV) enhancer, the α-globin 40 kb enhancer, SV40 enhancers, adenovirus enhancers, immunoglobulin enhancers, and T cell receptor enhancers. In addition, the enhancer corresponding to the promoter and/or transgene present in the construct are useful according to the invention.

Preferably, the β-globin HS3 COD is combined with a heterologous enhancer to achieve a level of transgene expression that is different from the level of transgene expression achieved using the complete β-globin LCR (i.e., consisting of HS1–HS4).

In the case of the β-globin 5'HS3-associated chromatin opening domain, in particular, a homologous COD/enhancer combination is particularly useful. That is, the 5'HS3 chromatin opening domain is combinable with the 5'HS2-associated fragment, which is active as an enhancer in erythroid tissue. Although the 5'HS3 domain alone confers chromatin opening activity on an associated transgene, and thus confers a non-physiological level of transcription, as defined above, it has been discovered that a construct consisting essentially of 5'HS3 and 5'HS2 operationally associated with a transgene provides for tissue-specific, integration site-independent expression of the transgene that is higher than the level of transgene expression in erythroid tissue using the 5'HS3 region alone.

The invention also encompasses vectors containing the LCR subregion chromatin opening domain, as described herein, and kits for reproducibly actuating expression of a transgene in a host cell, the kit containing DNA comprising an LCR subregion as described herein and container means therefore.

The invention also provides for methods for conferring integration site independence on a transgene integrated in single copy in the genome of a host cell comprising operably linking a domain, as defined above, to the transgene.

The transgene or expressible gene may be any desired gene, and is preferably a gene whose presence in a host cell corrects a genetic disorder. For example, globin-encoding genes, clotting factor-encoding genes, protein hormone-encoding genes, and ligand receptor-encoding genes. Particular reference is made to genes encoding proteins which have therapeutic utility, such as therapeutically useful proteins or ribozymes, or genes encoding anti-sense RNA.

Therapeutically useful proteins include anti-viral agents and decoy proteins useful in the prophylaxis or treatment of viral disease, especially diseases such as AIDS, as well as proteins which act to supplement or replace natural proteins that are defective. The use of transgenes expressing therapeutically useful intracellular antibodies is envisaged (see, for example, WO93/12232; WO94/02610).

The invention also provides a method for identifying a chromatin opening domain which comprises (a) providing a host cell containing a DNA construct in single copy, the construct comprising a candidate LCR subregion comprising a chromatin opening domain operably linked to an expressible reporter gene; (b) determining that the DNA construct reproducibly actuates transcription in the host cell by ascertaining transgene transcription for independent integration events in at least 3 separate genomes; and also may include the step of (c) comparing the amount of RNA encoded by the reporter gene with the amount of RNA encoded by an endogenous gene that is operably linked to an equivalent complete LCR endogenous to the host cell, wherein the presence of an LCR subregion comprising a chromatin opening domain is indicated if the amount of reporter gene-encoded RNA is less than about 80% of the amount of RNA encoded by the endogenous gene.

The invention also encompasses treatment of certain genetic diseases utilizing constructs according to the invention. For example, X-linked γ-globulinemia is treated by introducing a construct according to the invention into pre-B cells and introducing the transfected pre-B cells into a patient afflicted with X-linked γ-globulinemia. The construct includes the Bruton's kinase promoter and transgene operationally associated with a chromatin opening domain of the class II major histocompatibility complex (MHC) gene LCR. This chromatin opening domain will confer tissue-specificity corresponding to that of the full-length class II MHC LCR, and thus will direct transgene expression primarily in B or pre-B cells, and will also confer position-independent transgene expression of the full length LCR, but will not allow for expression of the transgene to the level conferred by the full length LCR. The reduced level of transgene expression conferred by the class II MHC chromatin opening domain will be less than about 60% of the level of expression of the transgene when associated with the full length corresponding LCR, will likely be less than about 40%, and may be on the order of about 10–25%.

As used herein, a "pre-B cell" refers to an immune system cell as defined in *The Leukocyte Antigen Fact Book*, 1993, Barclay et al., Eds., Academic Press, Harcourt Brace, London. A pre-B cell is thus defined by Barclay et al. as possessing the following cellular markers: CD9, CD10, CD19, CD20, CD22, CD24, CD38, CD40, CD72, CD74, and is surface Ig negative.

The invention also encompasses treatment of Gaucher's disease by introducing into a macrophage host cell a construct including the β-glucocerebrosidase transgene whose expression is initiated by the lysozyme gene promoter. The construct will also include the chromatin opening domain of the macrophage-specific lysozyme gene LCR. The macrophage-specific lysozyme chromatin opening domain will retain the tissue-specificity of the full-length lysozyme LCR, and thus will direct transgene expression primarily in macrophages, and will also retain position-independent transgene expression of the full length LCR, but will not allow for expression of the transgene to the level conferred by the full length LCR.

Preferably, the reduced level of transgene expression conferred by the macrophage-specific lysozyme chromatin opening domain will be less than about 60% of the level of expression of the transgene when associated with the full length corresponding LCR, will likely be less than about 40%, and may be on the order of about 10–25%.

This construct is used to treat Gaucher's disease by introducing transfected macrophages into a patient afflicted with Gaucher's disease. Expression of the wild type transgene in a patient afflicted with Gaucher's disease should result in correction of the diseased state.

As used herein, a "macrophage" refers to an antigen presenting, phagocytic cell as defined in *The Leukocyte Antigen Fact Book*, 1993, Barclay et al., Eds., Academic Press, Harcourt Brace, London. That is, a macrophage is defined in Barclay et al. as including the following cell surface markers: CD14, CD16, CD26, CD31, CDw32, CD36, CD45RO, CD45RB, CD63, CD71, and CD74. As used herein "macrophage" refers to either a resting cell or an activated cell, and thus may also possess the cell surface markers: CD23, CD25 and CD69.

The invention also encompasses treatment of genetic or transmitted diseases utilizing a chromatin opening domain as described herein. For example, the CD2 chromatin opening domain may be used in conjunction with an expressible gene to treat a T-cell associated disorder or disease. A T-cell associated disease or disorder is treated by introducing into a T-cell a construct including the CD2 chromatin opening domain and a gene encoding a protein for expression in T-cells, e.g., and interleukin, such as IL-2, a growth factor, or a viral determinant, such as an HIV determinant.

The invention further provides the use of a domain of the invention for the generation of transgenic mammals. In particular, the invention provides the use of such sequences for the generation of non-human transgenic mammals, which may be germ-line transgenic or somatic transgenics, especially transgenic mice, particularly for the purpose of drug development.

The invention is defined with respect to the following terms and definitions. As used herein, a "fully functional" or "complete" LCR is able to direct expression of a linked gene (which is termed a transgene when integrated into a host cell genome) to a "physiological" level, i.e., a level that is about equivalent to that observed for the endogenous gene that is associated with an equivalent endogenous LCR in the host cell. "About equivalent" refers to at least 80%, and preferably 95–100% of the expression level of the endogenous gene. Therefore, a "physiological" level of transcription or gene expression refers to any level that is equal to or above about 80% of the level of expression of the endogenous host cell gene.

A "fully functional" or "complete" LCR also refers to a region of DNA that includes all of the DNase I hypersensitive sites that are necessary to obtain at least 80–90%, and preferably 95–100%, expression of a linked gene when integrated into the genome of a host cell relative to a 100% expression level of a single copy of a gene that is under the control of an equivalent endogenous LCR in the host cell.

An "equivalent endogenous LCR" is defined as a region of DNA that confers copy number dependence and integration site independence on substantially the same coding region that the test LCR is associated within its native context. This coding region or gene naturally occurs in the host cell in association with the equivalent endogenous LCR. An equivalent endogenous LCR may refer to the complete LCR from which the LCR subregion is obtained; e.g., the human β-globin LCR could be considered an equivalent endogenous LCR for a human β-globin LCR subregion. Thus, a human β-globin LCR subregion may be tested in human erythroid cells with respect to the human β-globin LCR in the same type of human cells.

Alternatively, and often in practice, an equivalent endogenous LCR is the equivalent LCR that occurs in another species; e.g., where the host cell is a mouse cell and the introduced (test) LCR subregion and linked gene are the human β-globin LCR and gene, respectively, an "equivalent endogenous LCR" will be the mouse β-globin LCR and the endogenous gene will be the mouse β-globin gene. Thus, a β-globin LCR subregion may alternatively be measured by comparing the expression level of the human β-globin gene relative to the expression level of the mouse β-globin gene in mouse erythroid cells. The latter comparison is used only in those cases in which the two species of genes are expressed at equal levels in the two species of cells. The former comparison is made where equivalent gene expression levels are unobtainable across species.

Although the test LCR is measured with respect to its equivalent endogenous LCR in the host cell, the linked gene may be but need not be the same coding region as the endogenous gene. For example, where the host cell is a mouse cell and the test LCR and linked gene are the human β-globin LCR and the human CD2 gene, the test LCR/linked gene construct is measured in at least 3 transgenenic animals by comparing the amount of RNA coding for the linked gene (the CD2 gene in this example) to the amount of RNA coding for the mouse β-globin gene. Thus, in this example, expression of the human CD2 gene is stated in a percentage that is relative to expression of the mouse β-globin gene because both genes are under control of "equivalent", i.e., β-globin LCRs.

An "LCR subregion consisting essentially of a chromatin opening domain" is definable herein in its simplest terms as a region of DNA (that includes a chromatin opening domain) that is not a fully functional LCR in both structure and function.

Structurally defined, it is a subregion of DNA that is shorter in length than the fully functional LCR. "Shorter in length" may mean, for example, equivalent to as much as 80–90% of the length of an LCR, i.e., a region of DNA that has been determined to confer a physiological level of transgene expression, as defined herein, or a length which is only 50% or as little as 10%, 25% or 40% of the length of the complete LCR. However, because the actual length of an LCR chromatin opening domain subregion relative to the length of a "complete" LCR is not meaningful unless the minimum region of the "complete" LCR has been determined, a functional definition of this functional LCR subregion is also necessary for determining the presence of a chromatin opening domain.

Functionally defined, an LCR subregion consisting essentially of a chromatin opening domain retains the natural ability of the complete LCR when integrated with a transgene as a single copy construct to confer tissue-specific gene expression on the associated transgene, but does not possess the complete LCR's ability to confer "physiological" level expression on the transgene, but rather confers a level of transcription on the transgene that is somewhat lower than the full transcriptional activity naturally conferred by a complete LCR. As used herein, a "non-physiological level" of expression or transcription of the transgene refers to a level of expression that is less than about 80%, may be less than 70%, and may even be a value in the range of 5–50%, or for example, a value in the range of 1%–45%, relative to the level of expression of the endogenous host cell gene (i.e., a gene that is associated with an equivalent endogenous host cell LCR, as defined above). Of course, the level of expression of the endogenous host cell gene or the gene controlled by the equivalent fully functional LCR is arbitrarily set at 100%.

An LCR subregion of the invention also retains the ability of the complete LCR to confer integration site independent expression on the transgene; however, such site-independence is reproducibly retained only in the sense that the subregion allows for at least some (e.g., at least about 5%) expression of the transgene regardless of the integration site of the transgene in the host cell genome. The actual level of transgene expression may vary from one site to the next (e.g., it may vary from 1–45% among the different sites). Thus, as used herein, "reproducible" does not refer to an ability to confer a given level of transcription on a transgene, but rather to the ability to actuate transcription of a transgene independent of its integration site in a host cell genome. Thus, actuation of transgene expression is reproducible if the transgene is expressed in a minimum of three independent host cell genome integration events. An independent integration event may be represented, for example, by integration of a single construct into the genome of an $F_1$ generation transgenic animal, and thus three such events by three $F_1$ generation transgenic animals.

At its minimum functional definition, a chromatin opening domain that is not a fully functional LCR is a recombinant DNA that is a subregion of an LCR that consists essentially of a chromatin opening domain in that it reproducibly actuates integration site-independent transcription of a linked transgene, when the domain and linked transgene are present in single copy in a genome, and is hypersensitive to DNase I or endogenous nuclease, but does not contain other functional elements that may be contained within an LCR, i.e., enhancer activity. Thus, another functional test for open chromatin domain activity according to the invention is DNase I hypersensitivity. As described hereinbelow, DNase I hypersensitive site mapping may be performed on nuclear DNA from a given tissue of a transgenic animal containing the candidate chromatin opening domain in single copy. The presence of a chromatin opening domain will be indicated by the presence of a DNase I hypersensitive site at the site of integration of the COD/transgene construct in the chromosome.

"Enhancer" activity may be separated from "chromatin opening" activity even though both activities affect the expression level of the associated transgene. That is, enhancer activity boosts expression of the transgene but requires the presence of the chromatin opening domain. In contrast, chromatin opening domain activity allows for some transgene expression (i.e., at least 1%) that does not rise to physiological levels of expression in the absence of the enhancer element. The ability to convert chromatin to an open conformation is the key feature of an LCR subregion comprising a chromatin opening domain and refers to the ability of the subregion to reproducibly actuate a "non-physiological level" of expression of the linked transgene when the subregion/transgene construct is present in single copy in the host cell genome.

Although the level of gene expression that is conferred by an LCR subregion containing a chromatin opening domain may for some such LCR subregions appear to be an exceedingly low level (e.g., 1–5%) relative to the level of expression of the endogenous gene that is associated with an equivalent endogenous LCR, it is according to another comparison a significant level of expression of the transgene. For example, if transgene expression is compared in a first construct containing the transgene and an LCR chromatin opening domain subregion and a second construct containing a different LCR subregion that does not contain a chromatin opening domain, for example an LCR subregion that contains only an enhancer, the LCR subregion that contains the chromatin opening domain will confer significantly higher (e.g., 10-fold greater) transgene expression than an LCR subregion lacking a chromatin opening domain. For purposes of identification according to the invention, an LCR subregion that does not include a chromatin opening domain will confer less than about 0.1% transcription on a linked transgene when carried in as a single copy construct, with respect to endogenous gene transcription. For example, as described below, the β-globin chromatin opening domain confers an approximately 60-fold higher level of transcription on the β-globin transgene than the β-globin enhancer region alone confers on this transgene. Moreover, the β-globin enhancer region (e.g., HS2) alone confers expression on a transgene in a non-reproducible manner. As used herein, "significantly higher" may refer to a level of expression that is about 5-fold or higher, for example, 10-fold, 25-fold, 50-fold, or as much as 80–100-fold higher.

As used herein, "DNase I hypersensitive sites" are sites which are located in and around an expressed gene which are highly susceptible to cleavage by either DNase I or endogenous nucleases. As used herein, the term "hypersensitive" is inclusive of "super hypersensitive". A "DNase I hypersensitive site" refers to a region of DNA that is susceptible to DNase I at a concentration of at least 0.1 ug/ml at 37° C., which susceptibility occurs prior in time to susceptibility of the remainder of DNA (i.e., non-hypersensitive DNA) that is cleaved in a time course of incubation. Other concentrations of DNase I which may distinguish hypersensitive DNA from non-hypersensitive sites include, for example, 1–5 ug/ml, 10 ug/ml, or even higher concentrations such as 50–100 ug/ml DNase I. This variation in minimum DNase I concentration that distinguishes a hypersensitive site from non-hypersensitive DNA reflects the differing susceptibilities of different nuclear DNA preparations to nucleases. The presence of a "DNase I hypersensitive site" may be definitively determined by the appearance of a DNA fragment (i.e., a band) on a Southern blot due to preferential cutting of DNase I at a hypersensitive site.

Further features and advantages of the invention will become more fully apparent in the following description of the embodiments and drawings thereof and from the appended claims.

BRIEF DESCRIPTION OF THE DRAWINGS

The drawing will be briefly described.

FIG. 1C is a Southern blot analysis showing copy number determination in μD transgenic mouse lines containing the microlocus LCR construct GSE 1359 (Talbot et al., Nature 338:352–355, 1989). Southern blot analysis was performed on $F_1$ fetal head DNA digested with EcoR1 and hybridized to the βivs2 probe.

FIG. 1D is a Southern blot analysis showing loading controls of the same blot as FIG. 1C hybridized to an Apa1 digested mouse Thy-1 probe.

FIG. 4 is a map of the "I" transgene construct and ratios of transgenic/total numbers of mice generated by microinjection ($F_0$) or breeding ($F_1$). The open box represents the 1.9 kbp HindIII 5'HS3 fragment including the core region (FP1–3, striped box). The 1.9 kbp fragment was cloned into the polylinker 5' of the 800 bp human β-globin promoter and gene sequences (exons shown in small black boxes) in GSE 1758. B, BamH1; E, EcoR1; P, Pst1; S, Stu1 (only relevant sites shown). The horizontal black box represents the β-ivs2 probe region. Numbered arrows correspond to PCR primers described herein.

FIG. 5A is a Southern blot analysis of transgenic fetal head DNA showing copy numbers of transgenic mouse lines determined by analysis of $F_1$ fetal head DNA digested with BamH1 and hybridized to the βivs2 probe.

FIG. 5B is a Southern blot analysis showing loading controls of the same blot hybridized to an Apa1 digested mouse Thy-1 probe.

FIG. 8 is a map of the "B" transgene construct (not drawn to scale) and ratios of transgenic/total numbers of mice generated by microinjection ($F_0$) or breeding ($F_1$), and the number of founder lines generated. The grey box represents the synthetic 5'HS2 core region; horizontal black box is the βivs2 probe, numbered arrows correspond to PCR primers, as denoted herein. Bs, BsH1; B, BamH1; E, EcoR1; X, Xba1.

FIG. 9A is a Southern blot of transgenic fetal head DNA showing copy numbers of transgenic mouse lines containing the B construct of FIG. 8 determined by Southern blot analysis of $F_1$ fetal head DNA digested with EcoR1 and hybridized to the βivs2 probe. Both two copy lines contain 2 end fragments in Southern blots of BamH1 digestions (data not shown).

FIG. 9B is a Southern blot of transgenic fetal head DNA showing loading controls of the same blot as in FIG. 9A hybridized to an Apa1 digested mouse Thy-1 probe.

FIG. 10 is an autoradiogram showing results of S1 analysis of globin expression in fetal liver RNA of transgenic mouse lines containing the B construct of FIG. 8. Transgenic samples loaded in the same order as FIG. 9A. "Ntg." refers to non-transgenic; and "3X" to probe excess control.

DETAILED DESCRIPTION OF THE INVENTION

Figures 1A, 1B:
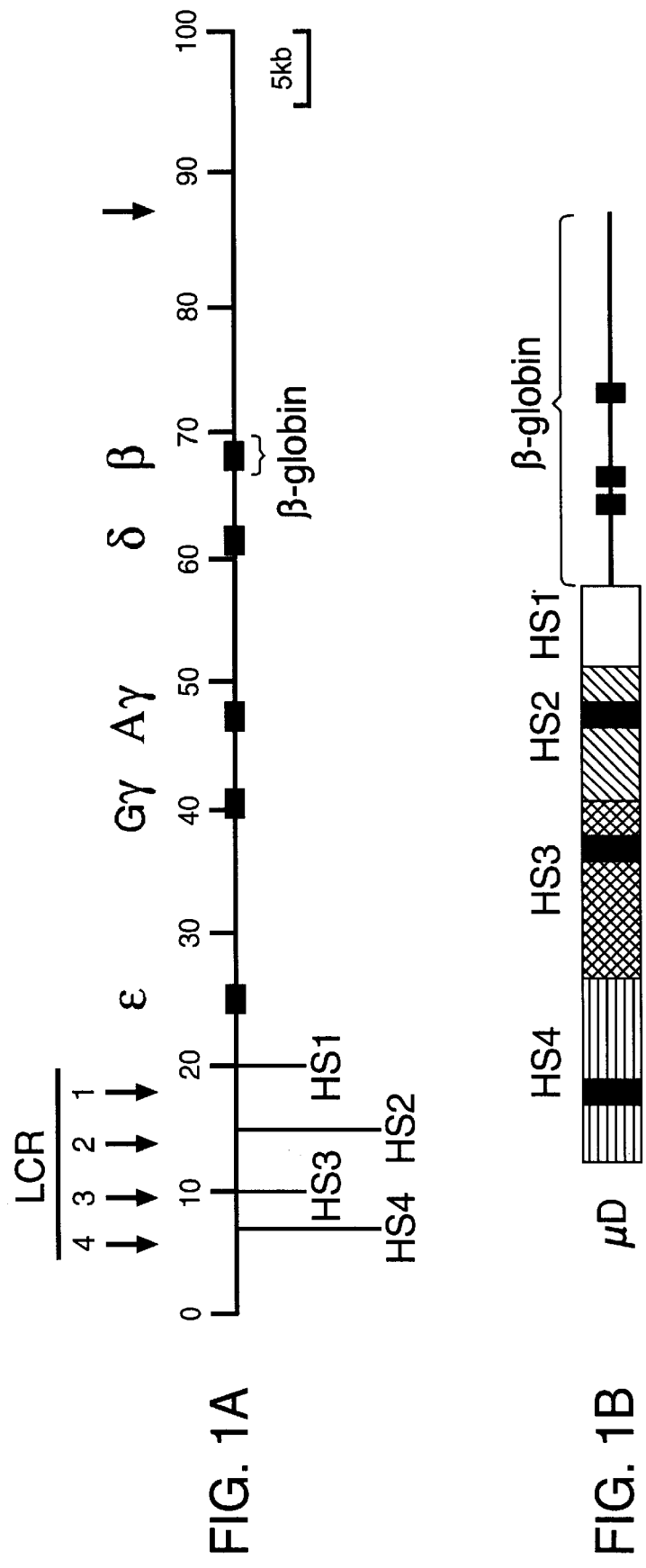
FIG. 1A is a schematic illustration of the β-globin locus.
FIG. 1B is a schematic illustration of the microlocus LCR construct, μD.

The invention is illustrated by the following nonlimiting examples wherein the following materials and methods are employed. The entire disclosure of each of the literature references cited hereinafter are incorporated by reference herein.

The invention is based on the discovery that certain functional properties of a locus control region may be physically and functionally separated. One such functional property is the ability of the LCR to transform the chromatin surrounding it into an open chromatin structure. The chromatin opening activity is essential in order to actuate transcription of an associated transgene regardless of the site of integration of the transgene in a host cell genome, but is in itself usually insufficient to give rise to physiological levels of transcription as the chromatin opening domains do not necessarily have enhancer activity. It is the identification and isolation of LCR chromatin opening activity that is the subject of the invention. The examples provided below enable identification and isolation of an LCR subregion containing a chromatin opening domain from any locus containing a tissue-specifically expressed gene that is under the control of Locus Control Region.

Example I provides methods that are generally useful in carrying out the invention, and that were used to identify and characterize the β-globin chromatin opening domain. Example II provides several LCR constructs that comprise fully functional LCRs. Example III teaches one of skill in the art how to identify and characterize an LCR subregion comprising a chromatin opening domain. The LCR subregion characterized in Example III is the 5'HS3 region. Example IV teaches one of skill in the art how to recognize an LCR subregion that does not contain a chromatin opening domain. Example V teaches one of skill in the art how to identify and characterize other chromatin opening domains of the invention in a reproducible and predictable manner.

Example VI teaches one of skill in the art how to use constructs of the invention. Example VII teaches one of skill in the art how to utilize the invention for gene therapy involving blood disorders. Example VIII teaches one of skill in the art how to utilize the invention for gene therapy involving cells of the immune system and malignant cells. Example IX teaches one of skill in the art how to utilize a chromatin opening domain in combination with a heterologous enhancer. Example X teaches one of skill in the art how to utilize the invention to treat Gaucher's disease. Example XI teaches one of skill in the art how to utilize the invention to treat X-linked γ-globulinemia. Example XII teaches one of skill in the act how to test for a chromatin opening domain using a reporter construct.

EXAMPLE I

Methods Useful in Carrying Out the Invention

The following methods are routinely used in the invention. These methods are stated in terms of the detailed experiments performed herein for identification and isolation of the β-globin HS3 chromatin opening domain. However, each method may be generalized by one of skill in the art for use in identifying and isolating other chromatin opening domains.

1. Generation of Transgenic Mice

Transgenic mice are generated by microinjection of about 0.25–0.50 ng/μl purified DNA, as described (Ellis et al., Sem. Dev. Biol., 4:359–369, 1993; Ellis et al., Eur. Mol. Biol. J. 12:127–134, 1993, both references of which are hereby incorporated), and screened by Southern blot hybridization and PCR on tail or fetal head DNA by standard procedures. Of the transgenic mice described below, 42 founder transgenic mice generated, 2 died, 3 were infertile, 2 failed to transmit, 1 transmitted only an incomplete transgene, and 8 transmitted in a mosaic manner. Sequences of PCR primers useful in β-globin locus fragment detection (see FIGS. 4 and 8) include:

1) 5'AAGCACAGCAATGCTGAGTCATG3' (SEQ ID NO: 1)
2) 5'TCAATGGGGTAATCAGTGGTGTC3' (SEQ ID NO: 2)
3) 5'GGGTGGGAGAATCAGGAAACTAT3' (SEQ ID NO: 3)
4) 5'GTCTTAGCCAGTTCCTTACAGCT3 (SEQ ID NO: 4)
5) 5'TGTCACATTCTGTCTCAGGCATC3' (SEQ ID NO: 5)
6) 5'TGCCAGATGTGTCTATCAGAGGT3' (SEQ ID NO: 6)
7) 5° CATGGTTTGACTGTCCTGTGAGC3' (SEQ ID NO: 7)
8) 5'GGTGGTTGATGGTAACACTATGC3' (SEQ ID NO: 8)

2. DNA Analysis

Southern transfer and hybridization are performed by standard procedures. Copy-number determination is performed using a Molecular Dynamic PhosphorImager and adjusted for loading differences or the presence of non-intact transgenes (observed after digestion with BspH1 or other diagnostic restriction enzymes). In order to determine definitively that a transgene is in single copy, it was found to be essential to examine end fragments in both directions. Digestions described below were therefore performed with Eco RI for the 5' end fragment and Bam HI for the 3' end fragment. Southern blots were probed with the βivs2 probe.

3. RNA Analysis

Fetal liver RNA (13.5–15.5 day) was extracted, 1 μg was hybridized to kinased double-stranded DNA probes, digested with 75 U S1 nuclease, and run on a 6% sequencing gel as described (Ellis et al., Sem. Dev. Biol., 4:359–369, 1993; Ellis et al., Eur. Mol. Biol. J. 12:127–134, 1993). Probe excess was demonstrated by including a sample containing 3 μg fetal liver RNA. Specific activities of human β-globin (Hβ) relative to the mouse βmajor (βmaj) probe was 2:1. The protected 160 nt Hβ and 95 nt βmaj bands were quantified on a Molecular Dynamics PhosphorImager and the % expression levels calculated according to the formula (Hβ/2βmaj)×100 to account for the specific activity differences. % Expression per copy was calculated as (2 βmaj genes/number Hβ transgenes)×% expression.

4. Vectors

Recombinant retroviral vectors as well as other DNA transfer schemes can be used in practice of the present invention. A recombinant viral vector of the invention will include DNA of at least a portion of a retroviral genome which portion is capable of infecting the target cells and a functional gene operatively linked thereto. As used herein, "functional" or "expressible" gene means a gene encoding a protein having a biological effect. By "infection" is generally meant the process by which a virus transfers genetic material to its host or target cell. Preferably, the retrovirus used in the construction of a vector of the invention is also rendered replication-defective to remove the effects of viral replication on the target cells. In such cases, the replication-defective viral genome can be packaged by a helper virus in accordance with conventional techniques. Generally, any retrovirus meeting the above criteria of infectiousness and capabilities of functional gene transfer can be employed in the practice of the invention.

Suitable retroviruses for practice of the invention include but are not limited to, for example, adenoviruses, adeno-associated virus and SV40 virus; suitable retroviral vectors include but are not limited to pLJ, pZip, pWe and pEM, well known to those skilled in the art; suitable packaging virus lines for replication-defective retroviruses include, for example, ψCrip, ψCre, ψ2 and ψAm.

It will be appreciated that when viral vector schemes are employed for gene transfer according to the invention, the use of an attenuated or a virulent virus also may be desirable.

The genetic material to be recombined with the retroviral vector or transferred through other methods of the invention is preferably provided through conventional cloning methods, i.e., cDNA, through overlapping sequences or any other suitable method yielding the desired clone.

An Adeno-Associated Virus (AAV) vector is representative of retroviral vectors useful according to the invention. AAV is a defective human parvovirus with no known pathogenicity. AAV contains a linear single-stranded DNA of 4.7 kb in length. The AAV genome carries two sets of functional genes: the rep genes, which encode proteins necessary for viral replication, and the structural capsid protein genes. AAV DNA also includes a 145 bp Inverted Terminal Repeat (ITR) at each end, between which lie the two sets of genes arranged in three major transcription units. Two transcription units overlap and encode a family of four related rep proteins, and the third encodes the virus capsid protein (Samulski, 1993, Curr. Opin. Genet. Devel. 3:74).

Knowledge of the AAV life-cycle has been applied to develop AAV based vectors and vector packaging cell lines for stably transducing mammalian cell lines. The principles of these systems are similar to those on which retroviral vectors are based (Muzyczka, 1992, Curr. Top. Microbiol. Immunol., 158:98). A plasmid harboring an expression cassette no greater than 4.7 kb in length and located between two AAV ITRs, is co-transfected with a plasmid encoding expressible AAV Rep and Capsid genes into a helper cell line productively infected with adenovirus. Culture supernatant from these transfectants is highly enriched for recombinant AAV virions containing single stranded DNA which encodes the expression cassette flanked by ITRs. When such virions are used in gene transfer experiments, stable transductants can be derived, and transduction is more efficient in cells passing through S-phase (Russell et al., 1994, Proc. Nat. Acad. Sci., 91:8915–8919), but integration of their recombinant genomes into host DNA appears to be random. To date, a number of AAV-based vectors packaged in this way have been used to stably transduce human T-lymphocytes, fibroblasts, nasal polyp, erythroid, and haemopoietic stem cells for gene therapy applications (Philip et al., 1994, Mol. Cell. Biol., 14:2411–2418; Russell et al., 1994, Proc. Nat. Acad. Sci., 91:8915–8919; Flotte et al., 1993, Proc. Nat. Acad. Sci., 90:10613–10617; Walsh et al., 1994, Proc. Nat. Acad. Sci., 89:7257–7261; Miller et al., 1994, Proc. Nat. Acad. Sci., 91:10183–10187). One of these reports describes the incorporation, into a helper-line-packaged AAV vector, of the β-globin Locus Control Region driving expression of the HbF γ chain gene, for possible use in gene therapy of Sickle Cell Disease (Miller et al., 1994, Proc. Nat. Acad. Sci., supra). See also PCT publication WO91/18088, by Chatterjee et al., for additional AAV-based eucaryotic vectors.

One advantage of using retroviral vectors, and in particular AAV vectors, is that foreign DNA introduced into mammalian cells remains attached to the AAV proviral genome and comprises a stable and heritable portion of the mammalian cell genome. Retroviral-mediated gene transduction into a cell according to the invention is optimized using a replication defective retrovirus.

Accordingly, a chromatin opening domain, as described herein, may be combined with a functional gene in an AAV vector. The vector is then administered to a patient, using a vector delivery system as described herein, to treat a disease which is associated with absence or mutation of the protein encoded by the functional gene. Administration of the vector will result in expression of the functional gene, in the cell into which the vector is introduced, in a position independent manner, the latter property being conferred by the chromatin opening domain.

5. Lipsomal Gene Transfer

Liposomes have been used for non-viral delivery of many substances, including nucleic acids, viral particles, and drugs. A number of reviews have described studies of liposome production methodology and properties, their use as carriers for therapeutic agents and their interaction with a variety of cell types. See, for example, "Liposomes as Drug Carriers," Wiley and Sons, New York (1988), and "Liposomes from Biophysics to Therapeutics," Marcel Dekker, New York (1987). Several methods have been used for liposomal delivery of DNA into cells, including poly-L-lysine conjugated lipids (Zhou et al., Biochim. Biophys. Acta. 1065:8–14, 1991), pH sensitive immunoliposomes (Gregoriadis, G., Liposome Technology, Vol I, II, III, CRC, 1993), and cationic liposomes (Felgner et al., Proc. Natl. Acad. Sci., USA, 84:7413–7417, 1987). Positively charged liposomes have been used for transfer of heterologous genes into eukaryotic cells (Felgner et al., 1987, Proc. Nat. Aca. Sci. 84:7413; Rose et al., 1991, BioTechniques 10:520). Cationic liposomes spontaneously complex with plasmid DNA or RNA in solution and facilitate fusion of the complex with cells in culture, resulting in delivery of nucleic acid to the cell. Philip et al. 1994, Mol. and Cell. Biol. 14:2411, report the use of cationic liposomes to facilitate adeno-associated virus (AAV) plasmid transfection of primary T lymphocytes and cultured tumor cells.

Delivery of an agent using liposomes allows for noninvasive treatment of diseases. Targeting of an organ or tissue type may be made more efficient using immunoliposomes, i.e., liposomes which are conjugated to an antibody specific for an organ-specific or tissue-specific antigen. Thus, one approach to targeted DNA delivery is the use of loaded liposomes that have been made target-specific by incorporation of specific antibodies on the liposome surface. Immunoliposome-associated reagents have been reported to result in less than optimal accumulation at target sites, possible due to sequestration by the reticuloendothelial system, primarily by the liver and spleen. Torchilin et al. (FASEB Journal 6:2716, 1992) report on enhancement of circulation times using polyethylene glycol-coated immunoliposomes. The invention will therefor encompass liposomal delivery of a DNA construct using such modified liposomes.

Liposomes are composed of a bilayer lipid matrix that wraps around an aqueous volume, thus isolating it from the external medium. The central aqueous core may vary in diameter from 20 nm to as much as 2–3 micrometers. The term "liposome", as used herein, is also intended to encompass liposomes which are composed of several (e.g., 2–3) concentric bilayers which define several individual aqueous compartments. Thermodynamically, liposomes have minimum free energy as long as the density of the phospholipids in each monolayer of the bilayer structure is the same.

Liposomes useful in the invention are composed of phospholipid molecules. A phospholipid molecule has a polar head group and two nonpolar, hydrophobic fatty acyl chains. In an aqueous environment, the most energetically stable form for phospholipids is within structures that allow the fatty acyl chains to avoid contact with water. A lipid bilayer is one such structure. Many phospholipids, when dispersed in water, spontaneously form lipid bilayer structures. Lipid bilayer structures useful in the invention are preferably circular structures.

The polar head group of the phospholipid molecule may include choline, e.g., lecithins (phosphatidylcholines) and sphingomyelins. Such molecules may also include amino groups, e.g., phosphatidylserine and phosphatidyl ethanolamine. Other polar head groups may include phosphatidylglycerol, phosphatidylinositol and cardiolipin.

An immunoliposome will include a liposome component, as described above, conjugated via its polar head group to the carboxy terminus of an immunoglobulin molecule. Fusion of an immunoliposome with the cell membrane will occur because most cell membranes are composed of protein and phospholipid bilayers. Immunoglobulins will be used for targeting liposomes to selected cells.

a) Preparation of Liposomes and Immunoliposomes

Liposomes and immunoliposomes may be prepared according to a variety of techniques, e.g., detergent dialysis or the formation of a water-in-oil emulsion, slow swelling in nonelectrolytes, dehydration followed by rehydration, dilution or dialysis of lipids in the presence of chaotropic ions, and mechanical preparation techniques such as freeze-thaw cycling.

Removal of detergent molecules from aqueous dispersions of phospholipid/detergent mixed micelles represents one way of producing liposomes (see J. Biol Chem. 246:5477 (1971) herein incorporated by reference). As the detergent is removed, the micelles become progressively richer in phospholipid and finally coalesce to form closed, single bilayer vesicles. Detergents commonly used for this purpose include bile salts and octylglycoside. Because this method does not involve the use of organic solvents and sonication, it is particularly useful for entrapping macromolecules, such as nucleic acids, which are sensitive to the presence of organic solvents or are structurally altered by sonication.

Another method of preparing liposomes is the reverse phase evaporation method detailed in U.S. Pat. No. 4,235,871, which is incorporated herein by reference. Liposomes prepared by this method have a typical average size of about 2–4 microns and are predominantly oligolamellar, that is, contain one or a few lipid bilayer shells.

Liposomes may also be prepared via hydration in the presence of a solvent. Multi-lamellar vesicles (MLVs) with high encapsulation efficiency can be prepared by hydrating the lipids in the presence of an organic solvent. The two phases are emulsified by vigorous mixing (vortexing) and then the organic phase removed by passing a stream of nitrogen gas over the emulsion. As the solvent evaporates, liposomes form in the aqueous phase.

Mechanical preparation methods, e.g., shaking by hand, sonication, French pressure freeze-drying, membrane extrusion, freeze-thawing, changing pH, calcium inducing, and micro emulsion techniques, have been used for the preparation of liposomes. In essence, a mixture of vesicle-forming lipids in a volatile organic solvent is deposited on the surface of a round bottomed flask, and the solvent is removed by rotary evaporation under reduced pressure. Vesicles ranging in size from one-tenth to tens of microns form spontaneously when an excess volume of aqueous buffer is added with agitation to the dry lipid.

Methods for controlling the size of liposomes are various and include extrusion and homogenization. One effective sizing method involves extruding an aqueous suspension of the liposomes through a series of polycarbonate membranes having a selected uniform pore size in the range of 0.2–0.6 micron, typically 0.1–0.2 micron. The pore size of the membrane corresponds roughly to the largest sizes of liposomes produced by extrusion through that membrane, particularly where the preparation is extruded two or more times through the same membrane. Extrusion of liposomes can also be performed through an asymmetric ceramic filter, as taught in U.S. Pat. No. 4,737,323, herein incorporated by reference. Other methods of reducing particle size include application of high pressures to the liposomes, as in a French Press, and homogenization of the liposomes.

Antibodies have been developed to cell-surface antigens for targeting of numerous cell types, including but not limited to malignant cells. Techniques are known for conjugating such antibodies to pharmacologically active agents or to labels to permit diagnosis, localization, and therapy directed toward such tumors.

Liposome targeting based on antibody/antigen recognition has been utilized in the prior art in the development of targeted delivery systems for delivery of various bioactive agents to a target site. Antibody-directed liposomes, or immunoliposomes, are used for this purpose. Antibody molecules are predominantly hydrophilic compounds with no affinity for the hydrophobic liposome membrane. Immunoliposomes can be used to deliver hundreds or more units of intraliposomal contents into an individual target cell. Immunoliposomes administered according to the invention are administered intravenously, intraperitoneally or directly to the target tissue or organ, at a dosage that is appropriate for the amount of biological agent or genetic material that is encapsulated by the liposome. Immunoliposome dosage will therefore vary from about 5 mg/kg body weight to about 1 gm/kg body weight, and may be in the range of 100 mg–500 mg/kg body weight.

As used herein, an immunoliposome comprises a liposome conjugated to an immunoglobulin molecule. Generally and as used herein, a liposome/immunoglobulin conjugate comprises an immunoglobulin molecule linked via direct or indirect means and either covalently or noncovalently to the phospholipid molecule. Generally, about 1 in every 200 phospholipid molecules of the liposome will be linked to an antibody molecule, with an acceptable range being 1 in every 20–20,000 phospholipid molecules of the liposome.

Where enhancement of specificity of the immunoliposome for the target site is desired, the immunoliposome may include antibodies of several different specificities, each cognate antigen being found at the target site. Such multiple specificity may also be conferred using bifunctional or trifunctional antibodies (see, e.g., U.S. Pat. No. 5,237,743, hereby incorporated by reference).

Methods are known in the prior art for preparing immunoliposomes. Immunoliposomes are prepared, for example, by adsorption of proteins (e.g., immunoglobulin) on the liposomal surface; incorporation of native protein into the liposome membrane during its formation (e.g., by ultrasonication, detergent dialysis or reverse phase evaporation); covalent binding (direct or via a spacer group) of a protein to reactive compounds incorporated into the liposomes membrane; noncovalent hydrophobic binding of modified proteins during liposome formation or by the incubation with preformed liposomes); and indirect binding, including covalent binding of immunoglobulin protein via a polymer to the liposome (see Torchilin, V. P. CRC Critical reviews in Therapeutic Drug Carrier Systems, vol. 2(1), hereby incorporated by reference).

Immunoliposomes may be prepared according to the following procedure.

1. Covalent Coupling of Antibody with NGPE.

0.6 mg N-Glutaryl phosphatidylethanolamine (NGPE) was dissolved in 0.5 cc 2-[N-morpholino]ethanesulfonic acid hemisodium salt (MES) buffer (in 0.016 M octylglucoside in 50 mM MES). After the addition of 4.8 mg 1-ethyl-3-(3-dimethylaminopropyl)carbodiimide (EDC) and 6 mg N-hydroxysulfosuccinimide (HSSI), the resulting mixture is incubated at room temperature for 5 min. The antibody solution (containing antimyosin antibody 2G42D7, described below, or other antibody) is then added (0.36 mg/ml). The pH of the mixture is then adjusted to 8.0 with 1M NaOH. The reaction mixture is incubated at 4° C. for 8–12 hour with mixing. The resulting NGPE-antibody conjugate is then dialyzed overnight against PBS, pH 7.4 to remove octylglucoside and other excess reagents.

2. Preparation of Immunoliposomes by Detergent Dialysis.

Liposomes are prepared from a mixture of egg phosphatidylcholine (PC) and cholesterol (Ch) in chloroform in the molar ratio 1:1. The lipid mixture (30 mg PC/17.96 mg Ch) is dried with argon, then vacuum dried for 2 hour and resuspended in 4 cc phosphate buffered saline (PBS) containing 0.016 M octylglucoside with brief ultrasonication. The solution of NGPE-modified antibody (0.7 mg/ml) is added to solubilized lipids. The mixture is dialyzed overnight against PBS (pH 7.4) to remove detergent. The resulting liposomes are extruded through a Nucleopore filter (0.6, 0.4, and 0.2 µm). The same method is used for preparation of liposomes without NGPE-antibody solution.

b) Loading of Immunoliposomes

Loading of compounds into liposomes may be achieved by one or more of a variety of active and passive methods. Passive loading by entrapment is employed where relatively low concentrations of the DNA construct is desired. Loading of high concentrations of DNA in liposomes may require active loading methods, e.g., as described in U.S. Pat. No. 5,129,549, herein incorporated by reference, in which a chemical gradient is created across the liposome membrane that results in trapping of the DNA in the internal aqueous phase of the liposome.

Liposome/DNA formulations are characterized by measurements of particle size, lipid concentration, and pH by standard methods as described above. DNA incorporation into the composition may be determined by inclusion of radiolabeled tracer in the composition. The amount of liposome-entrapped DNA is then determined by gel permeation chromatography using BioRad A-15M resin. The liposomal DNA fraction is calculated from the amount of radiolabel present in the void volume of the column, and the percentage of liposomal DNA from the ratio of label eluting in the void volume to the remaining label eluting from the column.

7. Preparation of Antibodies

Immunoglobulin molecules useful in the invention include whole antibody, or any antibody fragment, for example, a F(ab')2, Fab, and/or an Fv fragment of an antibody molecule. In addition, any variable region specificity of an antibody molecule is useful according to the invention.

A F(ab')2 fragment is that portion of an antibody molecule which contains the complete antigen-combining site, consisting of two light chains and part of each heavy chain, and is produced by enzymatic digestion, e.g., using pepsin, such that the heavy chain disulfide bonds remain intact in the F(ab')2 fragment. A Fab fragment consists of a single light chain and a part of a heavy chain disulfide bonded together. Fab is produced by enzymatic digestion, e.g., using papain, such that about one-half the F(ab')2 antigen binding fragment is generated. An Fc fragment is that portion of an antibody that is responsible for binding to antibody receptors on cells and the Clq component of complement. The Fc fragment is the portion of the antibody molecule that remains after papain digestion. An Fv fragment is that portion of an antibody consisting of the variable region of a Fab fragment.

Antibodies useful in the invention may be obtained through conventional polyclonal or monoclonal antibody preparation techniques. Antigen may be obtained from cells of the species toward which the antibodies are to be directed. Such species are preferably vertebrate, more preferably mammalian, and most preferably human. For antibodies directed toward human intracellular antigens, immortal cell lines represent a convenient source of such antigen.

To generate monoclonal antibodies, murine spleen cells from immunized animals are fused with an appropriate myeloma cell line. Fused cells are cultured in selective growth medium to establish hybridoma colonies, each colony secreting an antibody of interest. Culture supernatants from each colony are then tested for antibody specificity. Positive cultures are identified and expanded. See Kohler et al., Nature 256:495 (1975), hereby incorporated by reference.

8. Delivery of Gene via DNA-Protein Complexes

Transfer of a DNA construct according to the invention can be accomplished through many means, including but not limited to transfection using calcium phosphate coprecipitation, fusion of the target cell with liposomes, erythrocyte ghosts or spheroplasts carrying DNA, plasmid and viral vector-mediated transfer, and DNA protein complex-mediated gene transfer such as receptor-mediated gene transfer.

Receptor-mediated gene transfer is dependent upon the presence of suitable ligands on the surfaces of cells which will allow specific targeting to the desired cell type followed by internalization of the complex and expression of the DNA. One form of receptor-mediated gene transfer is wherein a DNA vector is conjugated to antibodies which target with a high degree of specificity cell-surface antigens (Wong and Huang, 1987, Proc. Nat. Aca. Sci. 84:7851; Roux et al., 1989, Proc. Nat. Aca. Sci. 86::9079; Trubetskoy et al., 1992, Bioconjugate Chem. 3:323; and Hirsch et al., 1993, Transplant Proceedings 25:138). Nucleic acid may be attached to antibody molecules using polylysine (Wagner et al., 1990, Proc. Nat. Aca. Sci. 87:3410; Wagner et al., 1991, Proc. Nat. Aca. Sci. 89:7934) or via liposomes, as described below.

Increased expression of DNA derived from ligand-DNA complexes taken up by cells via an endosomal route has been achieved through the inclusion of endosomal disruption agents, such as influenza virua hemagglutinin fusogenic peptides, either in the targeting complex or in the medium surrounding the target cell. An enhanced transfection protocol which allows for targeted delivery and uptake of nucleic acid vectors to specific cells at high efficiency, preferably in the absence of purification of the cells from a mixed cell population is described in PCT/GB94/01835.

Targeted gene delivery is also achieved according to the invention using a DNA-protein complex. Such DNA-protein complexes include DNA complexed with a ligand that interacts with a target cell surface receptor. Cell surface receptors are thus utilized as naturally existing entry mechanisms for the specific delivery of genes to selected mammalian cells. It is known that most, if not all, mammalian cells possess cell surface binding sites or receptors that recognize, bind and internalize specific biological molecules, i.e., ligands. These molecules, once recognized and bound by the receptors, can be internalized within the target cells within membrane-limited vesicles via receptor-mediated endocytosis. Examples of such ligands include but are not limited to proteins having functional groups that are exposed sufficiently to be recognized by the cell receptors. The particular proteins used will vary with the target cell.

Typically, glycoproteins having exposed terminal carbohydrate groups are used although other ligands such as antibodies or polypeptide hormones, also may be employed. Using this technique the phototoxic protein psoralen has been conjugated to insulin and internalized by the insulin receptor endocytotic pathway (Gasparro, Bio-chem. Biophys. Res. Comm. 141(2), pp. 502–509, Dec. 15, 1986); the hepatocyte specific receptor for galactose terminal asialoglycoproteins has been utilized for the hepatocyte-specific transmembrane delivery of asialoorosomucoid-poly-L-lysine non-covalently complexed to a DNA plasmid (Wu, G. Y., J. Biol. Chem., 262(10), pp. 4429–4432, 1987); the cell receptor for epidermal growth factor has been utilized to deliver polynucleotides covalently linked to EGF to the cell interior (Myers, European Patent Application 86810614.7, published Jun. 6, 1988); the intestinally situated cellular receptor for the organometallic vitamin $B_{12}$-intrinsic factor complex ahs been used to mediate delivery to the circulatory system of a vertebrate host a drug, hormone, bioactive peptide or immunogen complexed with vitamin $B_{12}$ and delivered to the intestine through oral administration (Russel-Jones et al., European patent Application 86307849.9, published Apr. 29, 1987); the mannose-6-phosphate receptor has been used to deliver low density lipoprotiens to cells (Murray, G. J. and Neville, D. M., Jr., J. Bio. Chem. Vol 225 (24), pp. 1194–11948, 1980); the cholera toxin binding subunit receptor has been used to deliver insulin to cells lacking insulin receptors (Roth and Maddox, J. Cell. Phys. Vol. 115, p. 151, 1983); and the human chorionic gonadotropin receptor has been employed to deliver a ricin a-chain coupled to HCG to cells with the appropriate HCG receptor in order to kill the cells (Oeltmann and Heath, J. Biol. Chem, vol 254, p. 1028 (1979)). Ligands selected from biotin, biotin analogs and biotin receptor-binding ligands, and/or folic acid, folate analogs and folate receptor-binding ligands to initiate receptor mediated transmembrane transprot of the ligand complex, as described in U.S. Pat. No. 5,108,921.

Generally, a ligand is chemically conjugated by covalent, ionic or hydrogen bonding to the nucleic acid. A ligand for a cell surface receptor may be conjugated to a polycation such as polylysine with ethylidene diamino carbodiimide as described in U.S. Pat. No. 5,166,320. DNA may be attached to an appropriate ligand in such a way that the combination thereof or complex remains soluble, is recognized by the receptor and is internalized by the cell. The DNA is carried along with the ligand into the cell, and is then expresssed in the cell. The protein conjugate is complexed to DNA of a transfection vector by mixing equal mass quantities of protein conjugate and DNA in 0.25 molar sodium chloride. The DNA/protein complex is taken up by cells and the gene is expressed.

Delivery of the foreign DNA into the target cell may also be achieved via the DNA construct's association with an endosomal disruption agent, such as the influenza hemagglutinin fusogenic peptide. The fusogenic peptide of the HA molecule is a modified form of HA which retains two important functions of HA. It allows for fusion of the targeted DNA/ligand complex to the cell membrane, but without the host cell sialic acid-binding specificity of the natural molecule. Instead, host cell binding specificity is conferred by the ligand/receptor interaction. The modified HA fusogenic peptide also retains the HA function of endosomal uptake, thus allowing for uptake of the complex into the host cell via membrane fusion, and the endosomal escape function of HA, which allows for escape of the enveloped DNA from the endosomal/lysosomal destruction pathway.

Thus, the invention encompasses a composition of matter for targeted delivery of DNA to a target cell. The composition comprises (a) a DNA construct containing an expressible gene encoding a protein of interest and a chromatin opening domain which domain confers position independent expression on the expressible gene; and (b) a ligand capable of binding to a target cell. Thus, the DNA construct will be complexed with the ligand such that when the ligand targets its cognate receptor on the target cell, the construct is physically carried along.

As described inter alia, the composition may further include (c) an endosomal disruption agent, for example an influenza hemagglutinin (HA) fusogenic peptide such as the HA amino acid sequence GLFGAIAGFIGAGTG-GMIAGGGC (SEQ ID NO:9).

The ligand may include an antibody that is specific for a surface antigen of the target cell. Such antibodies may include but are not limited to antibodies to any immune cell surface antigen, e.g., as are present on immune precursor cells, B-cells, T-cells, andmacrophages, i.e., CD19, CD20, CD21, CD22, CD38, CD72, MHCII, etc.

9. Target Cells

The cells targeted for transduction or gene transfer in accordance with the invention include any cells to which the delivery of the functional gene is desired, for example, immune cells such as T-cells, B-cells, macrophages, hematopoietic cells, and dendritic cells. Cells or cell populations can be treated in accordance with the invention in vivo or in vitro. Using established technologies, stem cells may be used in DNA transfection after enrichment procedures (see, for example, European Patent Applications 0 455 482 and 0 451 611, which disclose methods for separating stem cells from a population of hematopoietic cells). Alternatively, hematopoietic cells and stem cells may be made susceptible to DNA uptake using the method described in PCT/GB94/01835 which allows for targeted delivery and uptake of nucleic acid vectors to specific cells at high efficiency, preferably in the absence of purification of the cells from a mixed cell population. DNA may be transferred into B-cells or pre-B cells using published procedures; see, for example, Martensson et al., Eur. Jour. Immunol., 1987, 17:1499; Okabe et al., Eur. Jour. Immunol., 1992, 22:37; and Banerji et al., 1983, Cell 33:729). DNA is transferred into T-cells or cell lines via the procedure described in Philip et al., 1994, Mol. and Cell. Biol. 14:2411. DNA is transferred into macrophages as described in Immunol. and Cell Biol. 71:75, 1993.

In in vivo treatments, vectors of the invention can be administered to the patient, preferably in a biologically compatible solution or a pharmaceutically acceptable delivery vehicle, by ingestion, injection, inhalation or any number of other methods. The dosages administered will vary from patient to patient and will be determined by the level of enhancement of function of the transferred genetic material balanced against any risk or deleterious side effects. Monitoring levels of transduction, gene expression and/or the presence or levels of normal encoded protein will assist in selecting and adjusting the dosages administered. In vitro transduction is also contemplated within the present invention. Cell populations with defective genes can be removed from the patient or otherwise provided, transduced with a normal gene in accordance with the invention, the reintroduced into the patient.

EXAMPLE II

LCR Constructs That Comprise Fully Functional LCRs

Figure 2:
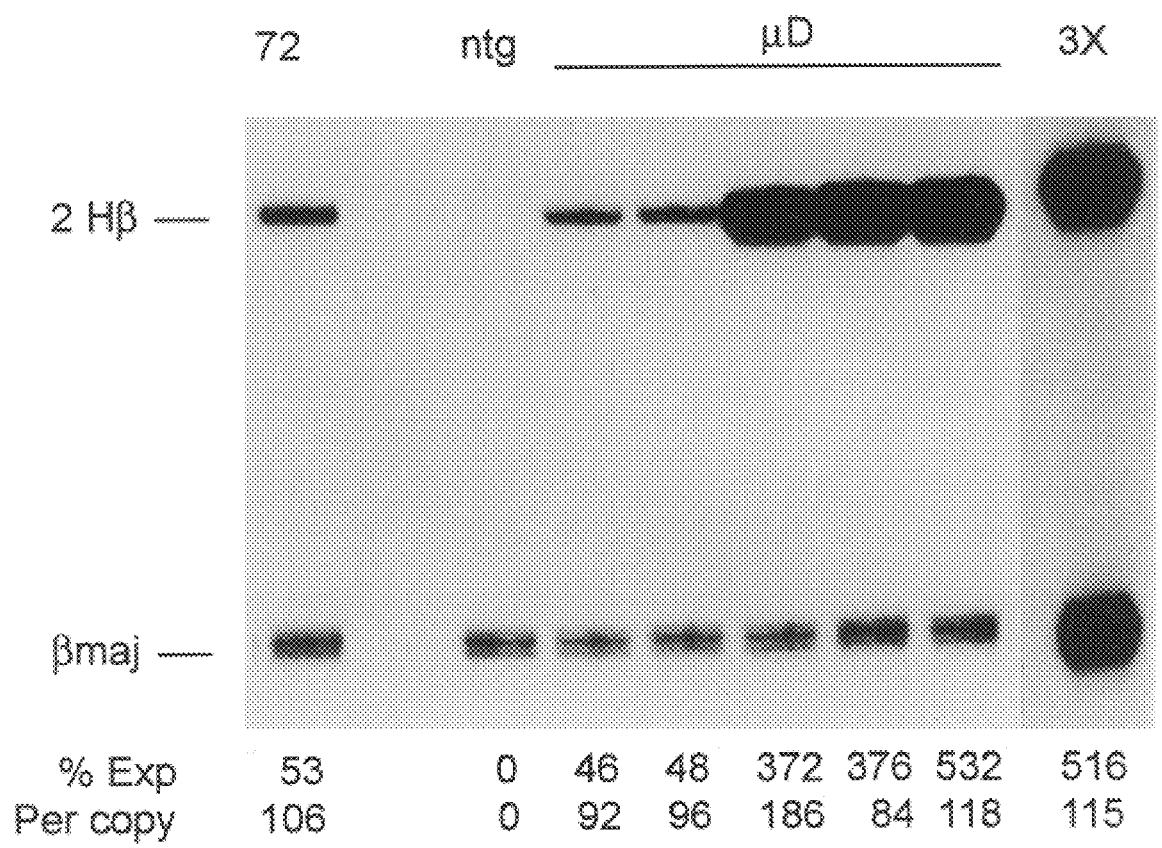
FIG. 2 is an autoradiogram of S1 analysis of globin expression in fetal liver RNA of βD transgenic mouse lines. Transgenic samples were loaded in the same order as FIG. 1C.

An LCR construct that comprises a fully functional LCR is identified and described in this Example. This construct functions at single copy and is of a reduced size compared to the significantly larger complete LCR construct known in the prior art (FIG. 1A–B). The microlocus LCR construct contains all four hypersensitive sites on a 6.5 kbp cassette upstream of the β-globin gene (FIG. 1B), it includes a 2.1 kb XbaI fragment encompassing DNase site HS1, a 1.9 kb HindIII fragment encompassing HS2, a 1.5 kb Asp718-SalI fragment encompassing HS3, a 1.1 kb partial SacI fragment encompassing HS4, and the 4.9 kb BglII fragment containing the β-globin gene, as described in U.S. Ser. No. 07/920, 536 and WO 89/01517. The complete DNA sequence of 16 kb of DNA 5' to the human β-globin gene is described in Li et al., 1985, Jour. Biol. Chem. 241:28;14901, hereby incorporated by reference. The microlocus construct was investigated with respect to whether it retained fully functional LCR activity. Eight $\mu D$ founder transgenic mice were generated containing the microlocus construct; five lines were established with a range of copy numbers from 1 to 9 (FIGS. 1C and D). S1 analysis of fetal liver RNA showed that both single-copy $\mu D$ lines expressed human β-globin at an average of 47% the level produced by the two mouse βmajor genes or 94% per copy (FIG. 2). In this case, the positive control "line 72" was calculated to contain 53% human β-globin or 106% per copy. Line 72 contains a single-copy of the entire human β-globin locus (Stouboulis et al., 1992, supra). These data demonstrate that the 6.5 kbp microlocus cassette fully activates single-copy β-globin transgene expression in a reproducible manner and therefore falls within the definition of a fully functional LCR. The β-globin microlocus LCR, when carried in single copy in a transgenic mouse line, is referred to as line $\mu D14$. The microlocus contains a chromatin opening domain that directs reproducible expression of independent single-copy transgenes, in addition to several enhancer elements, the combinations of elements of which provide for a physiological level of expression of the β-globin gene.

EXAMPLE III

Figures 3A, 3B, 3C:
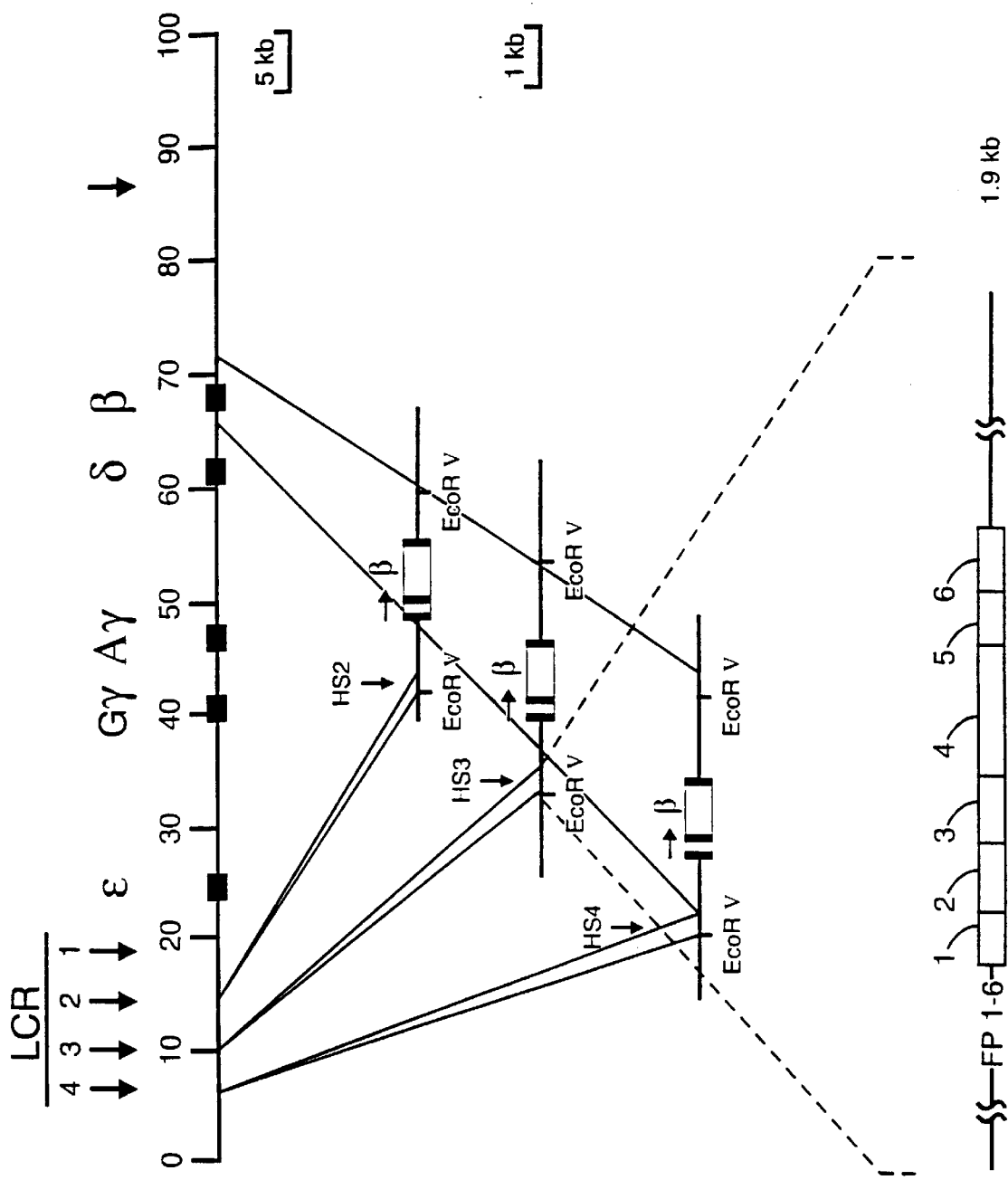
FIG. 3A is a schematic illustration of the β-globin locus showing the relative locations of the globin genes and DNase I hypersensitive sites 1–4.
FIG. 3B is a schematic illustration of three LCR subregion/transgene test constructs.
FIG. 3C is a schematic illustration of the 1.9 kb 5'HS3 region of the β-globin locus, showing the location of footprints 1–6 (FP1–6) within HS3.

How to Identify and Characterize an LCR Subregion Comprising a Chromatin Opening Domain A) Identification of the β-globin Chromatin Opening Domain FIG. 3A is a schematic illustration of the β-globin locus, showing the four DNase I hypersensitive sites that constitute the LCR. FIG. 3B illustrates three constructs tested herein in single copy transgenic animals for chromatin opening domain activity; i.e., each of the HS2, HS3, and HS4 domains operatively associated with the human β-globin gene. FIG. 3C illustrates the 1.9 kbp HS3 domain containing nuclear factor binding sites 1–6 (FP1–6) (not drawn to scale). In Example III, an LCR subregion comprising a chromatin opening domain is identified and defined. This subregion, identified and defined within the β-globin LCR, is the 5'HS3 domain. The results showed that the chromatin opening domain activity within 5'HS3 does not lie solely within the portion of the region of 5'HS3 known as the core region, i.e., corresponding to footprints 1–3 (see FIG. 3C). Nor is chromatin opening domain activity found within either of the 1.5 kbp 5'HS2 or 1.1 kbp 5'HS4 fragments, each of which contains a classical enhancer element. The HS2 and HS4 fragments are described in detail in PCT publication WO 89/01517, hereby incorporated by reference. HS2 is conveniently bound by HindIII sites to give a 1.5 kbp fragment; HS4 is bound by SacI sites to give a 1.1 kb fragment. In order to assess whether reproducible single-copy transgene expression activity requires all four hypersensitive sites in a microlocus arrangement or can be found within a specific smaller domain, the "C" construct (FIG. 4) which contains a β-globin gene regulated by the 1.9 kbp 5'HS3 fragment, was tested in single-copy in transgenic mouse lines.

Six founder mice were generated bearing the C construct and bred to wild-type mice to obtain nonmosaic $F_1$ fetuses representing 6 independent mouse lines (FIG. 4). FIG. 4 is a map of the C gene construct, and provides ratios of transgenic/total mice generated for $F_0$ or $F_1$ generations. In FIG. 4, transgenic mice were generated using 0.25 ng/$\mu l$ DNA as described (Kollias et al., 1986, supra; Ellis et al., 1993, supra; Ellis et al., 1993, supra). Screening of tail DNA by Southern blot analysis and PCR were by standard methods.

Five of the lines were shown to be single-copy as determined by the presence of unique 3' end fragments in Southern blot analysis of fetal head DNA digested with BamH1 and hybridized with a probe specific for human β-globin (FIG. 5). The copy number of these lines was verified by Southern blot analysis of 5' end fragments in EcoR1 digested DNA, and in all cases transgene intactness was shown by Southern blot analyses on Stu1-EcoR1 or Pst1 digested DNA (data not shown). Transgene intactness was further confirmed by PCR analysis of the β-globin 3' enhancer element using the primers whose locations in the construct are shown schematically in FIG. 4 (data not shown).

Figure 6:
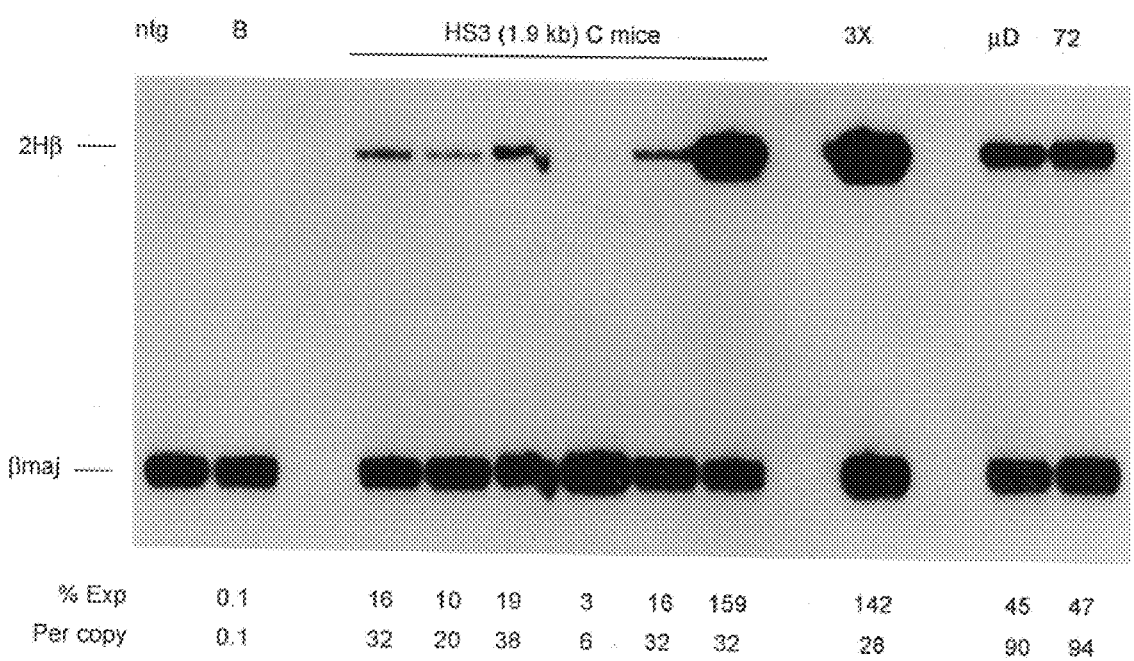
FIG. 6 is an autoradiogram of an S1 analysis of transgenic fetal liver RNA. C construct transgenic samples were loaded in the same order as in FIG. 5A. Ntg., non-transgenic; B, Transgenic Line B26 single-copy 5'HS2 construct; μD, Transgenic Line μD14 single-copy microlocus LCR construct; 72, Transgenic Line 72 single-copy 70 kbp β-globin locus construct; 3X, probe excess control.

S1 analysis was performed on 13.5 day fetal liver RNA to examine the expression status of the single-copy transgenes relative to the endogenous mouse 3-globin major genes (FIG. 6). In FIG. 6, 13.5 day fetal liver RNA was extracted and subjected to S1 nuclease analysis as described (Ellis et al., 1993, supra; Ellis et al., 1993, supra; Antoniou et al., 1988, supra). Specific activities of human β-globin (Hβ) relative to the mouse Bmajor (βmaj) probe was 2:1. The protected bands were quantified on a Molecular Dynamics PhosphorImager and the % expression levels calculated according to the formula (Hβ/2βmaj)×100 to account for the specific activity differences. % Expression per copy was calculated as (2 βmaj genes/number Hβ transgenes X % expression. As positive controls for expression, we used $F_1$ fetal liver RNA from Line 72 and Line μD14. Line 72 (complete β-globin LCR) and μD14 (β-globin microlocus) fetal liver expressed human β-globin mRNA at approximately 47% and 45% of the level produced by the two mouse βmajor genes, or 94% and 90% per copy respectively. As a negative control, we used nontransgenic (ntg) fetal liver RNA. In contrast to the full levels of expression produced by complete LCR constructs, β-globin transgenes alone express at less than 1% per copy (Ryan et al., 1989, supra).

Note that the B construct (FIG. 8), i.e., which contains a single-copy β-globin transgene regulated by the 1.5 kbp 5'HS2 fragment, does not express a detectable level of human β-globin, i.e., less than 0.1% per copy. This result demonstrates that the 5'HS2 enhancer element is suppressed by surrounding closed chromatin and hence is not an LCR element that possesses chromatin domain opening activity that functions in single-copy. However, the C lines containing the 1.9 kbp 5'HS3 fragment expressed significant human β-globin levels with a mean average of 26% per copy (range of 6–38% per copy) in all five single-copy lines. These data indicate that 5'HS3 is an LCR element that contains a chromatin opening domain which over-rides the suppressive effects of surrounding closed chromatin and reproducibly activates significant expression from independent integration sites.

Figure 7A:
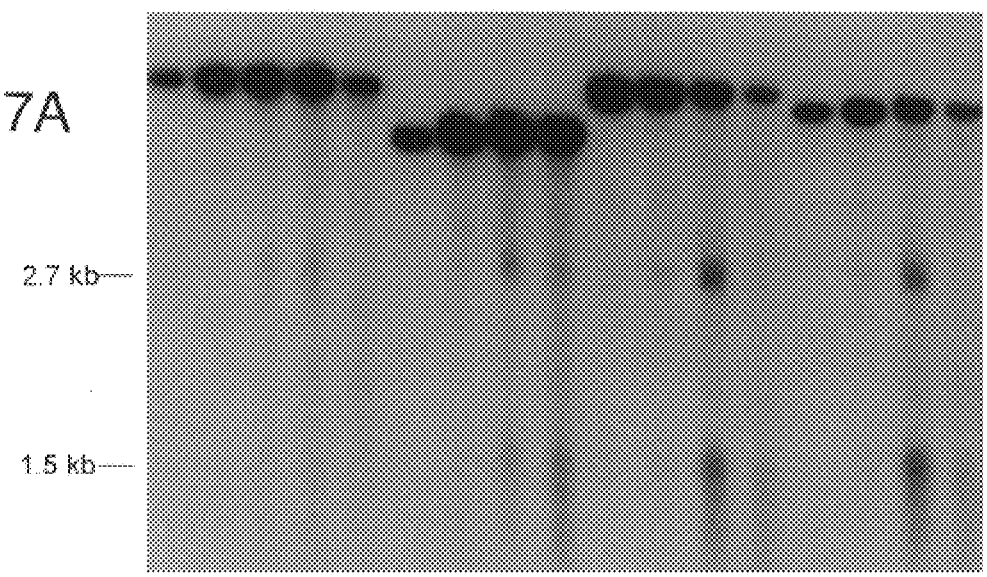
FIG. 7A is a Southern blot of results of DNase I hypersensitivity assays using DNA samples labeled B26, C8, C45 and C66 containing single-copy transgenes in 13.5 day fetal liver nuclei digested with DNase I and subsequently with EcoRI. The βivs2 probe was used. 0, zero time point; E, endogenous DNase.
Figure 7B:
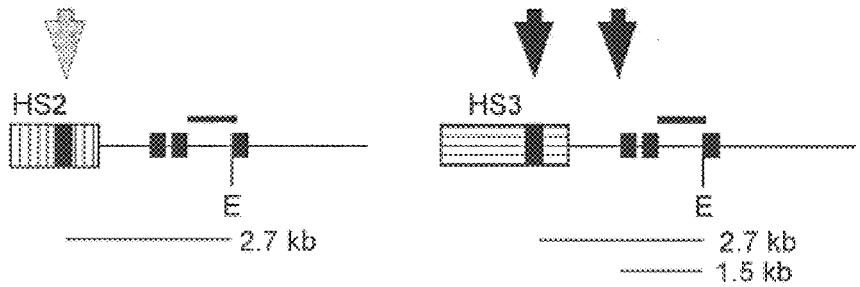
FIG. 7B is a schematic illustration of the location of DNase I hypersensitive sites (large arrows) within the integrated HS2 or HS3 construct. The black boxes within the HS2 or HS3 regions represent what is known in the art as the core regions. The black horizontal represents the βivs2 probe. The 2.7 kb and 1.5 kb-labeled horizontal lines represent the location of the fragments detected in FIG. 7A.

To investigate whether the 5'HS3 sequences in these lines are in an open chromatin conformation, we performed DNase I hypersensitive site mapping was performed on nuclei prepared from 13.5 day transgenic fetal livers obtained from three of the single-copy transgenic lines (data not shown), including the lowest expressing line C8 (FIG. 7A). FIG. 7B is a map of these hypersensitive sites. In FIG. 7A, 8–12 frozen transgenic fetal livers were pooled for each line and treated as described (Forrester et al., Genes Dev. 4:1637–1649, 1990). In brief, nuclei were prepared by 20 strokes of a B type Dounce pestle, and 100 μl resuspended nuclei aliquots each were digested with increasing volumes (0.5–12 μl) of 80 μg/ml DNase I (Sigma) for exactly 3 mins at 37°. Reactions were stopped, digested with Protease K, phenol/chloroform extracted, and ethanol precipitated. The DNA pellet was resuspended in 100 μl water after a 45 sec centrifugation, and 20 μl was digested with EcoR1 prior to Southern blot analysis and hybridization to the βivs2 probe as described (Kollias et al., 1986, supra). Autoradiography was for 4 days.

As expected for an expressing transgene, hypersensitive sites were observed at 2.7 kbp and 1.5 kbp 5' of the EcoR1 site in the β-globin transgene corresponding to the 5'HS3 core and the proximal β-globin promoter sequences, respectively. The C8 transgene is slightly more resistant to DNase I digestion than the other transgenes (FIG. 7A), suggesting that it is located in a particularly inaccessible chromatin region. Nevertheless, the C8 transgene chromatin contains the appropriate DNase I hypersensitive sites and the promoter is expressed. These data are consistent with the presence of a dominant chromatin opening activity residing in the 1.9 kbp 5'HS3 fragment that not only forms hypersensitive sites on the same sequences in the integrated transgene construct as those detected in the native chromatin context, but also reproducibly directs transgene expression.

Single-copy transgene expression is predictably and reproducibly directed by the 5'HS3 fragment. Although such expression varies among the constructs by as much as 6-fold per copy, the activation of transcription of the associated transgene is insensitive to position effects and hence is position independent. All the 5'HS3 lines express significant β-globin levels, and five of them express within a 2-fold range (between 20–38% per copy) Moreover, if one compares transgene expression for a transgene associated with a chromatin opening domain versus a transgene associated with an enhancer only, the lowest expressing 5'HS3 line produces 60-fold more β-globin mRNA than the non-expressing 5'HS2 line. Therefore, chromatin domain opening activity enables transcription of the associated transgene independent of the integration site of the domain/transgene construct in the host cell genome, but does not assume identical levels of transgene expression at each integration site.

B) Identification of a CD2 Chromatin Opening Domain

Studies of the function of the human CD2 gene 3' flanking region has revealed the presence of an LCR element which contains regions of tissue specific DNase I hypersensitivity. Deletional analysis of this region has shown that the LCR function is contained within the 2 kb of 3' flanking sequence immediately downstream of the human CD2 polyadenylation signal (Lang et al., 1991, Nucleic Acids Research 19:5851). These studies demonstrated a correlation between transgene copy number and level of specific mRNA within the thymus. Parallel studies using transient transfection assays have identified a 900 bp classical enhancer within this 2 kb region (Lake et al., 1990, Eur. Mol. Biol. Jour. 9:3129). Determination of the location of the chromatin opening domain within this 2 kb region of the CD2 locus is performed as follows.

Stepwise deletion of DNA of this 2 kb 3' flanking region is performed and the deleted constructs tested for loss of position independent transgene expression. Those constructs which retain position independent transgene expression, but which have lost full LCR activity and therefore do not express the transgene to the full expression level of the complete CD2 LCR (i.e., the 2 kb 3' flanking sequence) will contain the CD2 chromatin opening domain. The deletion constructs, and testing of the constructs for chromatin opening domain activity is described in detail below.

In order to further define the hCD2 LCR DNA sequences necessary for position independent expression, a series of 3' deletion constructs were used to generate transgenic mouse lines which are analysed at the DNA (Southern blot analysis), RNA (Northern blot analysis) and protein level (flow cytometry). The latter analysis allows an estimation of the quantity of protein expressed on the cell surface of individual thymocytes and T cells as measured by fluorescence intensity using a hCD2 monoclonal antibody. T cells are identified by concomitant staining for either Thy-1 or mouse CD4 and CD8. Transgene copy number is estimated by DNA hybridisation as previously described (Greaves et al., 1989 Cell 56: 979); quantitation of signal is done using a phosphorimager. A minimum of two sets of transgenic lines are compared, each carrying a single copy of each deletion construct. A positive control construct, in which position independent gene expression is retained, is the CD2 minigene linked to only 2 kb of immediate 3' flanking DNA. Position independent expression will be indicated at the DNA level and at the protein level in mature T cells. Similar analysis of thymocytes and T cells from lymph nodes will confirm this result (data not shown). In addition, hCD2 expression may be found on the thymocyte and T cell subsets defined by CD4 and CD8 expression (i.e. CD4−CD8−, CD4+CD8+, CD4+CD8− and CD8+CD4−).

Most LCRS defined to date have been shown to contain regions of tissue specific DNAse I hypersensitivity. Long range mapping has identified two regions of DNAse I hypersensitivity downstream of the hCD2 transgene in thymocytes (Greaves et al., 1989 Cell 56: 979). For localization of DNase I hypersensitive sites, DNA is extracted from transgenic thymocyte nuclei which had been treated with increasing concentrations of DNAse I. This DNA is then subjected to Southern blot analysis following digestion with HindIII which liberates the 2Kb of 3' DNA immediately downstream of the hCD2 polyadenylation signal. The blot is hybridised with a probe derived from the 5' end of the 2 kb region under investigation. A single large band will represent the parent 2 kb restriction fragment; smaller bands which appear only after incubation with increasing concentrations of DNAse I represent partial digestions of this fragment by DNAse I. Genomic molecular weight markers are used to estimate the size of these bands. These markers are obtained by digesting untreated hCD2 transgenic DNA with restriction enzymes thereby yielding fragments with a known range of predictable sizes which hybridise with the probes used.

The three DNase I hypersensitive sites in the 3' CD2 flanking sequence were localized in this way. The position of the HSS was verified by hybridising the same blot with a probe from the 3' end of the 2 Kb Hind III fragment. The upstream HSS cluster (HSS region 1) coincides with the region known to function as a classical enhancer (Lake et al., 1990, supra).

The function of the downstream HSS cluster (HSS region 3) is investigated by generating transgenic mouse lines in which these site is deleted, and by generating transgenic mouse lines in which this site is present.

1. Construction of transgenes

The generation of the 3' deletion constructs was as previously described (Lang et al., 1990, Nucleic Acids Research 19: 5851–5856), except in the case of the CD2 1.3 Kb transgene. The immediate 3' flanking 2 kb of hCD2 DNA was obtained by digesting a plasmid containing the hCD2 minigene linked to this 2 Kb fragment with BamHI (cuts distal to the polyadenylation signal) and HindIII (cuts 2 Kb 3' to the polyadenylation signal). The DNA obtained was gel purified and truncated further by digesting to completion with SacI (situated 1.5 Kb 3' to the polyadenylation signal). This 1.5 Kb fragment was purified and then partially digested with Afl II which yielded a 1.3 Kb fragment (which extended from the polyadenylation signal of the hCD2 gene to 1.3 Kb downstream). This fragment was purified after gel electrophoresis and ligated to a linearised and blunted plasmid (bluescript) containing the hCD2 minigene with 4.5 Kb of 5' flanking DNA and no 3' flanking DNA. The latter plasmid had been linearised with Bam H1—which lies immediately 3' to the polyadenylation signal. E. coli clones were selected after transformation and culture and the DNA obtained was screened (using asymmetric restriction enzyme digests) to ascertain the orientation of the 1.3 Kb fragment with respect to the hCD2 minigene. Both orientations (CD2 1.3 Kb and 1.3 Kb) were lifted out of bluescript with a Sal 1—Not 1 digest. The fragments were prepared for microinjection as described previously (Greaves et al., 1989, Cell 56: 979).

The generation and screening of transgenic mice is as described previously (Greaves et al., 1989, Cell 56: 979) using CDA/Ca, C57/Bl10 and CBAxC57/Bl10F$_x$ mice.

2. Flow cytometric analysis

For the evaluation of the pattern and level of hCD2 expression, $10^6$ thymocytes, mesenteric lymph mode cells or peripheral blood cells are incubated for 30 minutes at 4° C. with CD4 red (Boehringer Mannheim), CD8 PE (Catlag laboratories) and FITC conjugated anti-hCD2 (OKT11) antibodies. Lysis of red cells is done using Becton Dickinson lysis solution according to the manufacturers instructions. Cells are analysed using a Beckton Dickinson FACS sorter. Three color analysis is done using the Lysis II programme with a Hewlett Packard computer.

3. Preparation of Human CD2 positive and negative thymocytes from transgenic mice Thymocytes from 3 week old transgenic mice are obtained by teasing the thymuses in PBA (PBS with 1% BSA, Sigma). The human CD2 positive cells obtained are extracted, after 45 minute incubation with purified OKT11 mouse anti-human CD2 monoclonal antibody (a gift from Dr. Cantrell ICRF), using Dynal magnetic beads coated with Rat anti-mouse IgG1 using the procedure described by the manufacturer.

4. DNase I hypersensitivity mapping

Nuclei were extracted from both hCD2 positive, hCD2 negative or unsorted thymocytes and subjected to DNAse I digestion (Sigma) using the procedure described previously (Greaves et al., 1989, Cell 56: 979). The DNA extracted was subjected to Southern analysis (Southern, 1975, Journal of Molecular Biology 98: 503–517) following digestion with Hind III (for mapping within the full hCD2 gene) or BhlII (for mapping in the CD2 1.3 Kb transgenic lines). The nitrocellulose blots obtained were hybridised with either a) a $^{32}$p labelled hCD2 3' flanking probe extending from the polyadenylation signal 500 bp downstream or b) a 3'(NcoI-BamHI) or 5' fragment of the hCD2 cDNA. The blots were stripped and rehybridised with a 700 bp 3' endogenous Thy-1 probe—an Apa I fragment from the 4th exon—previously used to map hypersensitive sites within this locus [Spanopoulou Phd thesis]. They were analysed using autoradiography and a phosphorimager. All cellular manipulations were performed on ice apart from the DNAse I digestion which was done at 37° C.

The 1.3 and 1.5 kb portions of the 2 kb CD2 3' flanking region and the corresponding 0.7 and 0.5 kb portions, respectively, are tested in association with a transgene, as described above, in single copy transgenic mice. Where position independent transgene expression is retained in a shortened fragment, a chromatin opening domain is indicated if the level of transgene expression is less than about 60% of the level of transgene expression in association with the 2 kb CD2 LCR.

C) Identification of a Class II MHC Chromatin Opening Domain

A chromatin opening domain of the class II major histocompatibility complex (MHC) locus may be identified as follows. The MHC class II LCR is described in Carson & Wiles, 1993, Nucleic Acids Research 21:2065–2072. The chromatin opening domain of this LCR may be identified as described above for the β-globin and CD2 chromatin opening domains. Based on knowledge available in the art with respect to this LCR, the chromatin opening domain from the class II MHC will be smaller than the fully functional LCR described in Carson & Wiles, and larger than a fragment containing a deletion of three of the five DNase hypersensitive sites mapped in the MHCII LCR, as disclosed in Carson & Wiles, which deletion destroys LCR function.

The class II MHC chromatin opening domain will retain the tissue-specificity of the full-length class II MHC LCR, and thus will direct transgene expression primarily in B or pre-B cells, and will also retain position-independent transgene expression of the full length LCR, but will not allow for expression of the transgene to the level conferred by the full length LCR. The reduced level of transgene expression conferred by the class II MHC chromatin opening domain will be less than 60% of the level of expression of the transgene when associated with the full length corresponding LCR, will likely be less than 40%, and may be on the order of 10–25%.

D) Identification of a Macrophage-Specific Lysozyme Chromatin Opening Domain

A chromatin opening domain of the macrophage-specific lysozyme locus may be identified as follows. The chromatin opening domain of the macrophage-specific lysozyme LCR or the chromatin opening domain of the human lysozyme locus control region are described in Bonifer et al., 1990, Euro. Mol. Biol. Org. Jour. 9;2843; and Bonifer et al., 1994, Nucleic Acids Research 22:4202–4210.

A construct useful for testing for the presence of a macrophage-specific lysozyme chromatin opening domain may also contain the lysozyme gene promoter and a reporter gene. The chicken lysozyme LCR and promoter is carried on an 11.8 kb XhoI-SacI fragment from pIII.lyx construct as described in Bonifer et al., 1990 supra. This 11.8 kb fragment may be shortened to determine the location of its chromatin opening domain, as described herein, and the shortened fragment ligated to the reporter gene.

These chromatin opening domains may be identified according to the procedures used, as described herein, for localization of the β-globin chromatin opening domain. That is, the macrophage-specific lysozyme chromatin opening domain will retain the tissue-specificity of the full-length lysozyme LCR, and thus will direct transgene expression primarily in macrophages, and will also retain position-independent transgene expression of the full length LCR, but will not allow for expression of the transgene to the level conferred by the full length LCR. The reduced level of transgene expression conferred by the macrophage-specific lysozyme chromatin opening domain will be less than 60% of the level of expression of the transgene when associated with the full length corresponding LCR, will likely be less than 40%, and may be on the order of 10–25%.

EXAMPLE IV

How to Recognize an LCR Subregion That Does Not Contain a Chromatin Opening Domain An LCR subregion that does not comprise a chromatin opening domain and therefore does not fall within the claimed invention may be identified as follows. Three subregions of the β-globin locus, i.e., the so-called 5'HS2 and 5'HS4 regions encompassing β-globin enhancer elements (see FIG. 3A–B), as well as a portion of the 5'HS3 region known as footprints 1–3 (FP1–3, see FIG. 3C), were tested for chromatin domain opening activity and determined to lack this activity.

A small 5'HS2 core element has been shown to be a partial LCR that directs copy-number dependent expression of multicopy 5'HS2/β-globin transgene concatamers, but fails to direct expression of single-copy transgenes (Ellis et al., 1993, supra; Ellis et al., 1993, supra, both of which are hereby incorporated by reference).

The 5'HS2 construct, i.e., the "B" construct (FIG. 8), contains the wild-type 1.5 kbp Kpn1-Bg1I 5'HS2 fragment and thus includes the complete wild-type 5'HS2 fragment including the core and auxiliary factor binding sites in a fragment of about 1.5 kbp. The hypersensitive site was cloned into the polylinker 5' of the 800 bp human β-globin promoter or into the EcoRV site 3' of the human β-globin gene (exons shown in thick black boxes) in GSE 1758.

Founder adult transgenic mice were generated with the B constructs and identified by Southern blotting on tail DNA (FIG. 8). Because the $F_0$ generation copy number is difficult to establish reliably due to different cells containing different integration events and copy numbers, all 6 founder lines were bred to nontransgenic animals to obtain nonmosaic $F_1$ fetuses representing 6 different integration events (FIG. 8). The copy number of these lines was unambiguously determined by Southern blot analysis on fetal head DNA digested with EcoR1 and hybridized with probes specific for human β-globin (FIG. 9A) or mouse Thy-1 as a loading control (FIG. 9B). EcoR1 cleaves the transgene downstream of the probe and therefore single-copy transgenes will be visualized as an end fragment of random size, and higher copy numbers will usually contain one end fragment and a multicopy head-to-tail transgene concatamer. The copy number was verified for all lines by Southern blot analysis of Bam H1 digested DNA, and transgene intactness was confirmed by PCR analyses of the 5' and 3' ends (primer locations shown in FIG. 8; data not shown). Transgene intactness was further confirmed by additional Southern blots of BSpH1, and BamH1-Xba1 digested DNA for the B lines. By this process, we identified a range of copy numbers of intact transgenes including two single-copy lines for the B constructs.

S1 analysis was performed on fetal liver RNA to examine the expression status of the transgenes relative to the endogenous mouse βmajor genes. As a positive control, we used RNA from line 72 which contains a single copy of the entire human β-globin locus including the 20 kbp LCR fragment, and expresses human β-globin mRNA at about 50% the level produced by the two mouse βmajor genes or 100% per copy. In the S1 analysis shown in FIG. 10, human β-globin expression by line 72 was calculated to be at least 90% per copy. Globin genes that are not linked to LCR sequences express at less than 0.1% per copy.

The data shown in FIG. 10 indicates that the 5'HS2 construct is not sufficient to reproducibly obtain expression from a single-copy β-globin transgene. The results show that random integration of the construct into inactive or active regions of a chromosome result in undetectable and detectable transgene expression, respectively, but that detectable expression is not obtained in a predictable and reproducible manner. In FIG. 10, S1 analysis of fetal liver RNA from these mice detected human β-globin expression at less than 1% per copy in each of a single-copy and a two copy line, and 3% per copy in the 5 copy line. A level of 8% per copy was detected in one single-copy line and a level of 0% per copy in the other single copy line. The seven copy lines both expressed at about 23% per copy. These data demonstrate that the full length wild-type 5'HS2 fragment cannot reproducibly activate single-copy transgene expression. That is, if the 5'HS2/transgene construct randomly integrates into a region of chromatin that is open, and thus is expressed, then transgene expression may be randomly obtained in a single copy construct. However, if the same construct integrates into a closed region of DNA, then the 5'HS2 region is unable to open the chromatin and allow for transgene expression. Thus, reproducible chromatin opening activity is not found within the 5'HS2 region. Testing of the 5'HS4 construct (FIG. 3B) revealed similar results as the 5'HS2 fragment with respect to an inability to reproducible activate single copy transgene expression. In addition, other experiments demonstrated that footprints 1–3 of 5'HS3 core are unable to reproducibly activate single-copy transgene expression (data not shown).

MECHANISM OF ACTION

Without being bound to any one theory, it is postulated that the integration-site independence demonstrated by LCRs is attributable to two factors. First, an LCR is able to transform the chromatin surrounding it into an open chromatin structure. The chromatin opening activity is essential in order to actuate transcription regardless of the site of integration, but is in itself not sufficient to give rise to physiological levels of transcription as the chromatin opening domains do not necessarily have enhancer activity.

Secondly, an LCR contains powerful enhancer elements, which are not chromatin opening domains, which in single copy integrants cannot give rise to physiological levels of transcription when the enhancer elements are not associated with the LCR subregions of the invention. The level of enhancement is so high that any position effects due to the surrounding chromatin environment are effectively masked.

The chromatin opening domains of the invention, therefore, are capable of actuating transgene expression independent of the site of integration of the transgene into host cell chromatin. However, some chromatin opening domains of the invention, i.e., those which have been physically separated from an associated enhancer, are not able to confer reproducible physiological level expression because they do not possess the full level of transcriptional activity of a fully-functional LCR. The result is that, while significant expression is always observed, the level of such expression can vary more than that observed with an LCR which includes its enhancers.

Actuation of transcription occurs when a transgene is integrated in the form of open chromatin in the genome of the host cell. The transgene is always in a fundamentally active state and therefore susceptible to control by conventional transcription-regulating factors. In contrast, in the absence of the chromatin opening domains of the invention, transgenes often integrate into regions of chromatin which have a closed conformation, which confers a fundamentally inactive state on the transgene. There is thus a qualitative difference in the state of the transgene depending on the presence of a chromatin activating domain. In terms of quantitative expression, even the lowest levels of transcription observed when using the domains of the invention (6%) are substantially higher than the levels of expression observed without a chromatin opening domain (typically less than 0.1%).

The observed variation is a position effect and depends on the chromatin environment in which the transgene integrates. Thus, if the transgene integrates into a highly active chromatin region in the vicinity of a powerful enhancer, a physiological level of expression will be observed. Conversely, if the transgene integrates into a very inactive area of chromatin, as occurs in the majority of cases, the absence of enhancer function will mean that the level of expression observed will be lower than a physiological level.

In both cases, however, the presence of the chromatin opening domain will ensure that the transgene is expressible at physiological levels given the provision of appropriate enhancer functions.

The complete β-globin LCR is composed of multiple separable elements surrounding the four HS sites, 5'HS3 being responsible for the dominant chromatin opening activity of the LCR, and therefore being the primary regulator of transcription activation in vivo. 5'HS3 alone confers on average 26% expression per copy on single copy transgenes, i.e., a non-physiological level of expression, indicating that in the complete LCR additional transcriptional enhancer activity is provided by the other HS sites, including the 5'HS2 enhancer. Because chromatin domain opening activity is separable from enhancer activity, but enhancer activity is not evident without chromatin opening activity, enhancer activity can be said to be secondary or auxiliary to the essential chromatin opening activity of the 5'HS3 element.

The approach described herein for evaluating LCR sequences in single-copy transgenic mice provides a system for evaluating DNA elements that regulate mammalian gene expression. That is, in single-copy transgenic mice, enhancer and other LCR elements are functionally distinguishable. Moreover, expression from constructs designed for retrovirus or adeno-associated virus vectors can also be evaluated most reliably in single-copy transgenic mice. By including a dominant chromatin opening domain, such as that residing in 5'HS3, in a gene construct, it should be possible to express every single-copy vector integration event in a desired tissue.

EXAMPLE V

How to Identify and Characterize Other Chromatin Opening Domains of the Invention An LCR subregion comprising a chromatin opening domain may be identified and isolated by one of skill in the art using techniques known in the art and described herein according to the following method of identification and isolation.

One of skill in the art would be able to determine if a chromatin opening domain exists in a region of DNA by performing the following testing procedure. First, a region of DNA that is suspected of containing chromatin opening domain activity is isolated. Such a candidate region would, of course, reside within a locus control region. Locus control regions are associated with tissue-specifically expressed genes, and have been identified and isolated for several different loci, as discussed above. One criterion for the identification of a chromatin opening domain within a locus control region is its association with a DNase I hypersensitive site. Minimally, a chromatin opening domain will be associated with one such site; however, the domain may be associated with several such sites, for example, two, three or four hypersensitive sites, depending upon the length of DNA which the domain occupies and the number of hypersensitive sites clustered near or within the domain. A candidate chromatin opening domain may be provided, for example, as a fragment of DNA (e.g., a restriction fragment) from a known and isolated locus control region. Therefore, several candidate domains may be provided and tested simultaneously simply by digesting an LCR into two or more fragments, each fragment being an LCR subregion.

Second, once a candidate chromatin opening domain is provided as a DNA fragment, the fragment may be linked to a reporter gene to generate a construct. The reporter gene will be expressible in that it will be operably associated with a promoter that allows for gene expression. The reporter gene may be chosen by virtue of its encoding an easily assayable product, or it may simply be the gene that is naturally associated with the LCR from which the candidate chromatin opening domain is derived.

Third, the construct is then introduced into a host cell, usually, but not always, a mammalian host cell. The host cell may be a cell line that is carried in culture, and therefore the construct will be introduced via known procedures such as transfection, transduction or microinjection into a cultured host cell line without selection; e.g., using retroviruses. Alternatively, the host cell may be cells of a transgenic animal, in which case the construct is introduced into the animal using known procedures for making transgenic animals, as disclosed herein. Once the construct is introduced into the host cell, it then integrates into the host cell genome, and the reporter or test gene is known as a transgene.

Fourth, the candidate chromatin opening domain is then tested in those cells containing a single copy of the transgene for chromatin opening domain activity. As described in detail herein, a chromatin opening domain reproducibly actuates transcription of a transgene with which it is associated. Thus, in order to ascertain reproducible actuation of transcription, one of skill in the art would test a number of transgenic cell lines or transgenic animals, each cell line or animal representing an independent integration event, for expression of the transgene. Actuation of transgene transcription is considered reproducible, and thus integration-site independent, if the transgene is expressed in three different transgenic cell lines or transgenic animals. However, more than three cell lines or animals may be tested.

The actual level of expression of the transgene in the transgenic cell line or animal will be determined by measuring the amount of RNA expressed by the transgene, as described in detail herein, and comparing that amount to the amount of RNA expressed by the endogenous host cell gene. The endogenous host cell gene will be defined by virtue of its association with an endogenous LCR that is considered equivalent to the LCR from which the candidate domain is derived. An equivalent endogenous LCR is not difficult to identify and is defined in the Summary of the Invention above. The amount of test gene RNA is measured as a percentage of the amount of endogenous gene RNA. The percentage is arrived at by forming a ratio of the amount of test gene RNA over the amount of endogenous gene RNA times 100. Of course, differences in specific activities of the two RNAs must be taken into account. Therefore, for instance, if the specific activity of the test gene RNA is twice that of the endogenous gene RNA, then the amount of endogenous gene RNA is multiplied by two prior to calculating the percentage: (test gene RNA/2×endogenous gene RNA)×100. This simple formula (I) provides the total expression levels of test gene and endogenous gene in a host cell.

The results may also be expressed according to a slightly different formula. That is, since the test gene may be introduced in single copy or multiple copies in the host cell genome, and the endogenous gene is normally present in two copies in the host cell genome, the results may also be expressed as expression of single copy of endogenous gene per single copy of test gene. This is calculated as two endogenous genes divided by the number of transgenes, multiplied by the percent expression: (2×endogenous gene/× number test genes)×(% expression=I).

The candidate chromatin opening domain is determined to possess chromatin opening domain activity according to two criteria. First, the RNA comparison must provide results which show that the candidate domain reproducibly provides at least a minimum level of test gene expression (i.e., minimally, equal to or above a 1% level), but does not provide the full level of expression conferred by the complete LCR (i.e., less than full level expression corresponding to less than about a 90% level). This level of test gene expression will be reproducible because it occurs independent of the integration site of the test gene in the host genome. Therefore, a candidate chromatin opening domain will be considered to fall within the first criterion defining a chromatin opening domain if the expression of the test gene is reproducibly between 1% and 80% of the level of expression of the endogenous gene.

The second criterion for defining a chromatin opening domain relates to the ability of the domain to "open" the chromatin in the region of the test gene. Such opening activity is determined by DNase I hypersensitivity. That is, if the candidate domain possesses a DNase I hypersensitive site both in its native context and in its non-native context integrated in the host cell genome, then it falls within the second criterion defining a chromatin opening domain.

DNase I hypersensitivity is defined above in the Summary of the Invention. A DNA fragment is considered to possess a DNase I "hypersensitive site" if the fragment contains a site that is preferentially cut in a DNase I sensitivity assay. Preferential cutting is usually ascertained by detecting a DNase I-cut band in a Southern blot. A DNA fragment lacks a DNase I hypersensitive site where preferential cutting does not occur; i.e., instead of detecting a discrete band after digestion with DNase I, a smear of lower molecular weight DNA may be detected representing random cutting events at longer incubation times or higher concentrations of DNase I. Although the parameters for performing DNase I sensitivity assays may vary, e.g., the DNase I concentration, specific activity, and temperature and time of digestion, the identification of hypersensitive sites (as distinguishable from sensitive sites) is well-known and well-practiced in the prior art, and thus will be routine identification using variations on the above parameters.

In order to fall within the definition of chromatin opening domain, as defined herein, a candidate domain must fulfill both the first and second criteria described above, that is, the domain must reproducibly confer expression on the test gene when the domain/test gene construct is carried in single copy in the host cell genome, the test gene expression being about 1–80% of endogenous gene expression, and the domain must be associated with one or several DNase I hypersensitive site(s).

EXAMPLE VI

How to Use Constructs of the Invention

Use of an LCR subregion containing a chromatin opening domain, as described herein, is particularly desirable for the following reasons. First, because the LCR subregion/transgene construct is smaller than the full-length LCR, methods of transfer of the construct are useful that were not previously possible using full-length LCR constructs. These methods include the use of viral vectors, which allow for transfer to an animal of an LCR subregion/transgene construct but not for a much larger full-length LCR/transgene construct. Thus, production of a transgenic animal solely at the animal embryo stage by microinjection of the construct is not required by the invention. This represents a considerable advantage where a large transgenic animal, e.g., a cow or bull, is produced, as it is difficult to produce such animals via embryo microinjection techniques but not via viral infection.

Second, the use of LCR subregion/transgene constructs allows for tissue-specific production of a desired protein by virtue of the tissue-specific nature of transgene expression conferred by the domain.

Third, the use of constructs of the invention allow for production of a controlled non-physiological level of the trans-protein by virtue of the integration-site independence of transgene expression conferred by the domain and the ability of the transgene to express when integrated in single copy.

The invention thus provides domains for use in medicine; that is, for use in the manufacture of human proteins from animals.

An LCR subregion comprising a chromatin opening domain may be used for production of therapeutically useful proteins in a number of ways, as follows.

For example, an LCR subregion of the invention may be used in transgenic animals where integration-site independent expression of a transgene is desired. In addition, it may be desirable to produce a protein in a specific tissue, e.g., blood tissue or mammary tissue, using a single copy of the protein-encoding gene.

For example, where it is desirable to produce human β-globin in blood tissue of a transgenic animal, a chromatin opening domain of the invention, e.g., the HS3 domain, linked to the human β-globin gene, may be transferred to the animal either using conventional transfer of genetic material at the early embryo stage or using viral transfer vectors. A level of human β-globin that is less than the physiological level of the animal's β-globin may be necessary, for example, to obtain proper processing or glycosylation of the foreign protein. A non-physiological level of human β-globin may be obtained by transferring the HS3/human β-globin construct described herein to the animal and purifying human β-globin from the animal's blood tissue.

Similarly, where it is desirable to produce human growth hormone in a transgenic animal, the level of growth hormone produced in the animal must be carefully controlled due to the deleterious effects of over-production of the hormone. Such control may be achieved by transferring a chromatin opening domain of the invention coupled to a gene encoding human growth hormone to an animal genome without concern for whether the construct will integrate into an inactive position in the genome. The inventive domain will open the chromatin at the site of integration of the construct in the host cell genome to allow for expression of the human growth hormone gene at a controlled level. Human growth hormone may then be purified from the transgenic animal.

In addition, for example, where it is desirable to produce a human blood clotting factor, e.g., human factor VIII, IX or von Willebrand factor, in the mammary tissue of an animal, or other proteins, e.g., albumin, lactoferrin, a transgenic animal may be produced using a chromatin opening domain coupled to the gene encoding the factor. The factor may then be purified from milk produced by the animal.

Methods for producing transgenic animals via germ line or viral transfer events, e.g., mice, pigs, chickens, sheep, cows, bulls, etc., are well-known and documented in the art. A domain of the invention also is useful in gene therapy-related applications, for example, when a gene construct comprising a domain of the invention is integrated in single copy into the genome of a host cell.

At present, in order to definitively test expression levels from a potential gene therapy construct, the construct must be inserted into an integration competent viral vector, transferred into a helper cell line to assemble stable high-titer virus, and then successfully transduced into mouse hematopoietic stem cells (for review see Miller, Nature 357:455–460, 1992). Long-term repopulation of mice by the infected stem cells finally produces mature differentiated cells that can be assessed for expression of the transduced gene.

An alternative method is to test expression from a potential gene therapy construct present in transgenic mice at a single copy before the difficulties of assembling a high-titer virus are confronted. In the case of β-globin vectors, expression is evaluated in erythroid cells derived from stem cells that contain the construct as a single-copy transgene, and only those β-globin constructs that express appropriately and reproducibly need be packaged into virus for use in gene therapy.

Since the discovery of LCRs, LCRs have been indicated for use in gene therapy. LCR subregions of the invention are also useful for gene therapy, for example, treatment of cardiovascular diseases, AIDS, inherited or acquired genetically based diseases, hemaglobinopathies, cystic fibrosis, severe combined immune deficiency diseases, lysosomal storage disease, muscle diseases, etc. In the case of the β-globin 5'HS3 region, in particular, gene therapy treatments of diseases associated with blood tissue disorders are useful.

One difficult aspect of gene therapy is reproducibly obtaining high-level, tissue-specific, and long-term expression from genes transferred into stem cells (for reviews see Mulligan, Science 260:926–932, 1993; Dillon, Trends Biotech. 11:167–173, 1993). LCRs confer such position-independent activation on transgenes. Additional important considerations are that the gene system used should be as compact as possible, in view of the need to package the gene into available delivery systems as well as the need to minimize possible adverse effects on the genome of the recipient cell, and furthermore that the gene should be active in single copy in the host cell genome. This latter consideration is important because many viral systems currently proposed for the delivery of therapeutic genes integrate in single copy in host cells. Thus, LCR subregion/transgene constructs of the invention allow for carefully controlled expression of the transgene because they allow for single-copy gene expression.

The following examples provide specific uses of a construct according to the invention.

EXAMPLE VII

Targeted Delivery of Chromatin Opening Domain Construct to Treat Hemoglobin Disorders, Sickle-Cell Anemia and Thalassemia Blood disorders such as severe hemoglobin (Hb) disorders, sickle cell anemia and thalassemia are treatable according to the invention using a retroviral vector comprising the chromatin opening domain from the β-globin locus control region and a human γ-globin gene. Miller et al. (1994 supra) describes infection of CD34+ human hematopoietic cells with a recombinant rAAV construct containing the human γ-globin gene the HS2, HS3, and HS4 sites of the human β-globin locus, and subsequent expression of the γ-globin gene.

The present invention contemplates use of the HS3 site from the β-globin locus in a gene therapy construct to obtain position independent expression of a functional gene to treat a blood disorder. Chromatin opening domain-containing constructs of the invention can thus be used to transfer a globin gene into repopulating stem cells with subsequent expression in erythroblasts in vivo.

A human β-globin COD construct useful for treatment of a blood disorder may be prepared as follows. The human β-globin COD (fragment HS3), and the $^A\gamma^*$ globin gene (Sorrentino, B. P. (1990) Ann. N.Y. Acad. Sci. 612, 141–151) are subcloned into pUC007 (Ney, P. A. (1990) Genes Dev. 4, 993–1006). A Bgl II/Sal I fragment of this construct is subcloned into pUC008 (Walsh, C. E. (1992) Proc. Natl. Acad. Sci. USA 89, 7257–7261), which is then digested with Nhe I and ligated to the Xba I fragment of pSUB201. The pSUB201-derived AAV inverted terminal repeats will flank the human β-globin COD. The plasmid construct is cotransfected with the complementing plasmid, pAAV/ad (Samulski, R. J. (1989) J.Virol. 63, 3822–3828) into 293 cells previously infected with adenovirus type 5 to make the recombinant AAV. Preparation of cell lysates containing rAAV, Hirt extracts, and Southern blot analyses are described in Walsh, C. E. (1992) Proc. Natl. Acad. Sci. USA 89, 7257–7261; Samulski, R. J. (1989) J. Virol. 63, 3822–3828; Hirt, B. (1967) *J. Mol Biol.* 26, 365–369. Any portion of the globin gene may be used as a probe. All rAAV cells lysates are concentrated by ultrafiltration using a model 8400 stir cell apparatus and XM300 membrane (Amicon) prior to heat inactivation of adenovirus (56° C., 30 min). The final volume of concentrated cell lysate will be ≈1 ml per 10-cm$^2$ dish of 293 cells used for cotransinfection.

rAAV particle titer is estimated as follows. A variation of previous assays (Samulski, R. J. (1989) J. Virol. 63, 3822–3828) may be used to estimate particle number. Twenty microliters of rAAV cell lysate is incubated (37° C., 1 hr) with 200 units of DNase (Boehringer Mannheim) in a final volume of 200 µl (20 mM Tris-HCl, pH 8.0/10 mM MgCl$_2$ buffer). DNase-protected particle (DPP) viral DNA is extracted with RNA STAT-60 (Tel-Test, Friendswood, Tex.) using the manufacturer's protocol with a final volume of 20 µl. This technique favors recovery of the low molecular weight single-stranded DNA genome of the rAAV vector particles. The polymerase chain reaction (PCR) will generate a fragment spanning the junction between HS3 and the $^A\gamma^*$ globin gene in the recombinant globin locus. PCR conditions are as follows: 23 cycles; 95° C./1 min, 58° C./1 min. 72° C./1.5 min; 5' primer, 5'-TCTTCAGCCTAGAGTGATGAC (SEQ ID NO:10); 3' primer, 5'-ATAGTAGCCTTGTCCTCCTC (SEQ ID NO:10).

CD34$^+$ selected progenitor cells are prepared and transduced as follows. Human peripheral blood mononuclear cells are obtained by hemapheresis of a patient with Hb SS disease. A Ceprate kit (CellPro, Bethell, Wash.) is used for CD34$^+$ cell enrichment according to the manufacturer's protocol. One thousand CD34+selected cells are exposed to 500 µl of rAAV-containing cell lysate (10$^6$ particles) in a total volume of 1000 µl of tissue culture medium (Dulbecco's modified Eagle medium, 15% fetal calf serum, 50 ng of interleukin 6 per ml, and 100 ng of stem cell factor per ml). After an overnight exposure with gentle rocking at 37° C. in 5% CO$^2$, the cells are resuspended to 10$^3$ cells per ml and plated at 1000 cells per plate in methylcellulose containing growth factors (10 ng of granulocyte/macrophage colony-stimulating factor per ml, and 5 units of erythropoietin per ml). Cells are incubated at 37° C. in 5% CO$_2$ for 13–19 days prior to analysis of progenitor derived colonies.

The COD construct is transferred and expressed as follows. RNA extraction from individual colonies is performed by placing each colony (<10 µl of methylcellulose) in 250 µl of Stat-60 (Tel-test) according to the manufacturer's protocol and maintained at −70° C. until reverse transcriptase PCR (RT-PCR) analysis. RT-PCR reagents and the thermal-cycle are obtained from Perkin-Elmer. The reverse transcriptase reactions (42° C./30 min, 95° C./5 min) are performed as single or double volume mixtures, followed by single or matched PCRs (35 cycles; 95° C./1 min. 60° C./1 min) using the appropriate primers. RNA-derived PCR mixtures, which included [$^{32}$P] CTP, are electrophoresed on 10% denaturing polyacrylamide gels and dried prior to autoradiogram or Phosphorimager analysis. Comparison of the polyacrylamide gel band intensities is made using the densitometry function of a Phosphorimager (Molecular Dynamics) High-performance liquid chromatography HPLC is used for Hb analysis as described (Fibach, E. (1993) *Blood* 42, 162–165).

A construct according to the invention, containing a chromatin opening domain from the β-globin locus, an expressible γ-globin gene, and a means for delivering this DNA to a target cell, e.g., recombinant AAV, is useful for delivering a single copy of the γ-globin gene to such cells to restore a globin deficiency. For example, the construct described above may be used to treat sickle cell anemia, wherein there exists a deficiency of normal globin due to the presence of a mutation in the globin gene which consists of a single amino acid substitution. In individuals who are homozygous for the sickle hemoglobin abnormality, this single amino acid substitution brings about aggregation of hemoglobin molecules into polymers when the oxygen tension is lo, thus distorting the normally pliable discoid red cells into a charcteristic sickled shape. A construct of the invention comprising a chromatin opening domain may be used to restore normal globin synthesis in that the integration of a single copy of the construct would result in synthesis of a level of normal globin that is significantly lower (e.g., 25%) than if the complete LCR were present, but sufficient in amount to prevent the aggregation of defective globin molecules which results in cell sickling.

Alternatively, a construct of the invention that comprises a chromatin opening domain could be used to treat thalassemias, which are characterized by deficient synthesis of the α- or β-globin chains. A chromatin opening domain is particularly useful in the context where a non-physiological level, i.e., less than the normal amount, of synthesis of a protein occurs. For example, a construct containing the β-globin COD and the α- or β-globin gene may be used to restore synthesis of the α- or β-globin chains in that the presence of a single copy of the construct should be sufficient to produce enough α- or β-globin to bring the amount of that molecule to normal (physiological) levels within the cell.

EXAMPLE VIII

Targeted Delivery of Chromatin Opening Domain Construct to Primary T Lymphocytes and Primary and Cultured Tumor Cells In this Example, a DNA construct containing a chromatin opening domain and an expressible gene, according to the invention, can be delivered to lymphocytes and tumor cells using an AAV-based plasmid, containing AAV terminal repeats, and cationic liposomes as carrier molecules. This delivery system is described by Philip et al., Molecular and Cellular Biology, 1994, 14;2411. This system takes advantage of the simple carrier system of lipofection and the stable inheritance capability of the AAV plasmid. Therefore, any construct according to the invention may be delivered to a selected group of cells utilizing this complex of DNA and liposome. A chromatin opening domain derived from an LCR will be selected for its tissue specificity; i.e., a CD2 COD for T-cells, an MHC II COD from a class II MHC LCR for immune cells such as pre-B cells; a COD from a lysozyme LCR for macrophages. Delivery of a construct to primary T-cells and primary tumor cells, described below, is meant to be representative and not limiting as to cell type or tissue specificity.

A construct according to the invention may include a chromatin opening domain from the CD2 LCR. An approximate 2.0 kb region of the CD2 locus is described in Lang et al. (1991, Nucleic Acids Res. 19;5851). This 2.0 kb region has been shown by Lang et al. to be sufficient for position independent and copy number dependent expression of the CD2 gene in a transgenic context. That is, this 2.0 kb region of the CD2 locus is fully functional LCR. The chromatin opening domain of the CD2 LCR may be localized by testing regions of the 2 kb fragment for position independence, as disclosed herein. Once localized, the CD2 COD may be inserted into the plasmid pSSV9/CMV-IL2, described in Philip et al., 1994, supra. This plasmid contains the human interleukin-2 (IL-2) gene and the immediate-early promoter-enhancer element of the human cytomegalovirus (CMV) flanked by AAV terminal repeats. Where a reporter gene is desired or useful, the CD2 COD may be inserted into the plasmid pA1CMVIX-CAT (Philips et al., 1994 supra), which contains the CMV immediate-early promoter enhancer sequences and some intervening sequences with splice acceptor sequences derived from an immunoglobulin G variable region (pOG44; Strategene, La Jolla, Calif.), the bacterial chloramphenicol acetyltransferase (CAT) gene, and the simian virus 40 late polyadenylation signal flanked by AAV terminal repeats in a pBR322 vector. Plasmid DNA is isolated by alkaline lysis and ammonium acetate precipitation followed by treatment with DNase-free RNase, phenol-chloroformisoamyl extractions, and ammonium acetate precipitation (Ausubel et al., Current Protocols in Molecular Biology, John Wiley & Sons, Inc., New York, 1993).

The rat prostate cell line R3327 and bladder cell line MBT-2 (ATCC) are maintained in RPMI 1640 medium supplemented with 5% fetal bovine serum (FBS). Cell line 293 is a human embryonic kidney cell line that is transformed by adenovirus type 5 (Graham et al., J. Gen. Virol. 36:59–72, 1977). This cell line is grown in Dulbecco modified Eagle medium supplemented with 10% FBS.

Primary lung, ovarian, and breast tumor cells are obtained from the solid tumors of patients. The tumor samples are minced into small pieces and digested in 200 ml of AIM V medium (GIBCO, Grand Island, N.Y.) supplemented with 450 U of collagenase IV (Sigma, St. Louis, Mo.) per ml. 10.8 Klett units of DNase I (Sigma) per ml, and 2,000 U of hyaluronidase V (Sigma) per ml (Topolian et al., J. Immunol. 102:127–141, 1987). After 1 to 2 h of digestion, cells are homogenized with a glass homogenizer (Bellco, Vineland, N.J.). Cells are washed three times in DPBS-CMF (Whittaker, Walkersville, Md.) Lymphocytes are separated from nonlymphoid cells by capture on a MicroCELLector-CD5/8 device (Applied Immune Sciences (AIS), Santa Clara, Calif.). The microCELLectors are polystyrene devices containing covalently immobilized monoclonal antibodies for selection of T cells. Nonadherent cells (mainly tumor cells) are removed and cultured in RPMI 1640 medium supplemented with 2 mM L-glutamine, 100 U of penicillin-streptomycin per ml. and 10% FBS. Tumor cells are cultured for 2 to 4 weeks prior to transfection.

Peripheral blood mononuclear cells from healthy controls are isolated from buffy coats (Stanford University Blood Bank, Stanford, Calif.) by using Lymphoprep (Robbins Scientific, Sunnyvale, Calif.). T cells or T-cell subsets are further isolated with AIS MicroCellectors. Briefly, peripheral blood mononuclear cells are resuspended at $15 \times 10^6$ cells per ml in 0.5% Gamimmune (Miles, Inc., Elkhart, Inc.) and loaded onto the washed CD3, CD4, or CD8 AIS MicroCELLectors. After 1 h. nonadherent cells are removed. Complete medium (RPMI 1640 medium [Whittaker] containing 10% FBS, 2 mM L-glutamine, and 100 U of penicillin-streptomycin per ml) is added to the adherent cells in the MicroCELLectors. After 2 to 3 days in a 5% $CO_2$, 37° C. humidified environment, adherent cells are removed and prepared for transfection.

Small unilamellar liposomes are prepared from the cationic lipid dimethyldioctadecylammonium bromide (DDAB) (Sigma) in combination with the neutral lipid dioleoylphosphatidylethanolamine (DOPE) or cholesterol (Avanti Polar Lipids, Alabaster, Ala.). Lipids are dissolved in chloroform. DDAB is mixed with DOPE or cholesterol in either a 1:1 or 1:2 molar ratio in a round-bottomed flask, and the lipid mixture was dried on a rotary evaporator. The lipid film is rehydrated by adding sterile double-distilled water to yield a final concentration of 1 mM DDAB. This solution is sonicated in a bath sonicator (Laboratory Supplies, Hicksville, N.Y.) until clear. Liposomes are stored at 4° C. under argon.

For the preparation of recombinant AAV (rAAV) stocks, 293 cells are split and grown to approximately 30 to 50% confluence. At this time, the cells are infected with adenovirus type 5 and incubated at 37° C. After 2 to 4 h, the infected cells are cotransfected with 10 µg of plasmid and 10 of the rep capsid complementation plasmid, pΔBal, per 100-mm-diameter tissue culture dish ($0.5 \times 10^7$ to $1 \times 10^7$ cells). Calcium phosphate coprecipitation is used for transfection (Hermonat et al., Proc. Natl. Acad. Sci. USA 81:6466–6470, 1984). At 12 to 18 h after transfection, the medium is removed from the cells and replaced with 5 ml of Dulbecco modified Eagle medium containing 10% FBS. At 48 to 72 h posttransfection, AAV is harvested as follows. The cells and medium are collected together and freeze-thawed three times to lyse the cells. The medium-cell suspension is then centrifuged to remove cellular debris, and the supernatant is incubated at 56° C. for 1 h to inactivate adenovirus (Hermonat, supra; Tratschin et al., Mol. Cell. Biol. 5:3251–3260, 1985). After heat inactivation, the viral supernatant is filtered through cellulose acetate filters (1.2-µm pore size). Viral stocks are then stored at −20° C. rAAV stock containing a $10^4$ viral titer is used to infect cells.

Cellular transfection is performed as follows. For primary tumor cells and tumor cell lines, $10^6$ cells are plated in 2 ml of serum-free medium per well of a six-well dish. Plasmid DNA (10 µg) is mixed with 30 nmol of total lipid as liposomes composed of DDAB and DOPE in a 1:2 molar ratio. Serum-free medium (0.5 ml) is added to the liposome-DNA complex, which is then transferred to the cells. The cells are incubated at room temperature for 5 min. and then fetal calf serum is added to the cells to yield a final concentration of 5% fetal calf serum. For T cells, $5 \times 10^6$ to $10 \times 10^6$ cells are plated in 1 ml of serum-free medium per well of a six-well dish. Plasmid DNA (50 µg) was mixed with 100 nmol of total lipid as liposomes composed of DDAB and DOPE or cholesterol in a 1:1 molar ratio. The transfections are then performed as above.

IL-2 is assayed as follows. Cells are counted, $10^5$ cells are plated in 1 ml per well of a 24-well plate. The following day, supernatants are collected and assessed by using a Quantikine IL-2 enzyme-linked immunosorbent assay (ELISA) kit from R & D Systems (Minneapolis, Minn.). IL-2 levels are expressed as picograms per mililiter of the supernatant.

Intracellular IL-2 is assayed as follows. Transfected cells are stained at various time points for intracellular IL-2 protein levels by a modified flow cytometry procedure (Jung, et al., J. Immunol. Methods 159:197–207, 1993). Cells are harvested, washed with DPBS-CMF (Whittaker) and resuspended at $10^6$ cells per ml in cold 1% paraformaldehyde (Sigma) in DPBS-CMF for 10 min at 4° C. Cells are washed with DPBS-CMF and resuspended in cold DPBS-CMF containing 0.1% saponin 9sigma) and 10% FBS (HyClone, Logan, Utah) for 10 min at 4° C. Cells are then washed with cold saponin buffer and stained with mouse anti-human IL-2 antibody (Genzyme, Cambridge, Mass.) for 15 min at 4° C. Cells are washed with cold saponin buffer and stained with a fluorescein isothiocyanate-conjugated goat anti-mouse F(ab')$_2$ second-step antibody (Caltag, South San Francisco, Calif.) for 15 min at 4° C. After washing in saponin buffer, cells are washed with DPBS-CMF and resuspended at $10^6$ cells per ml for flow cytometric analysis. Flow cytometry is performed with a FACScan (Becton Dickinson, Milpitas, Calif.).

To measure CAT activity, the transfected cells are collected, washed twice with phosphate-buffered saline, and then resuspended in 0.25 M Tris. pH 7.8. Cell extracts are obtained by three consecutive freeze-thaw cycles followed by centrifugation at 16,000×g for 5 min. Protein concentrations of extracts are measured by a Coomassie blue G250-based assay (Bio-Rad. Richmond, Calif.), and protein concentrations were normalized. A volume of extract is added to 200 nmol of acetyl coenzyme A and either 0.1 (R3327 rat prostate cells) or 0.5 (T cells) µCi of [$_{14}$C]chloramphenicol (Amersham, Arlington Heights, Ill.). The reaction mixture is incubated at 37° C. for 16 h. The acetylated and unacetylated chloramphenicol species are extracted with cold ethyl acetate and resolved on silica thin-layer chromatography plates with 95:5 (vol/vol) chloroform-methanol solvent. The radiolabeled products are visualized by autoradiography.

For Southern analysis, chromosomal DNA is extracted from cells by the procedure described by Hirt (Hirt, B., J. Mol. Biol. 126:275–288, 1967). After digestion with appropriate restriction enzymes. 5 µg of DNA is loaded onto a 1% agarose gel, electrophoresed, and transferred to Hybond N+ (Amersham) nylon membrane. The membranes are hybridized with a 0.685-kb IL-2 gene fragment at 65° C. in rapid hybridization buffer with DNA fragments labeled with $^{32}$P by the random priming method (Megaprime DNA labeling kit: Amersham) and washed according to the manufacturer's instructions. Autoradiograms of these filters are exposed on X-ray film (type XAR: Eastman Kodak Co.) with intensifying screens at 70° C. for 1 to 4 days.

The above-described DNA/liposome/AAV delivery system is useful for delivering a construct in single copy to the genome of a cell in that it allows the viral coat and capsid to be replaced by liposomes, yet includes sufficient viral elements to allow for stable inheritance via recombination of the construct with the host cell genome. Delivery of DNA by this means does not require interaction of the delivery vehicle with any specific cell surface receptor.

A construct according to the invention, containing a CD2 COD to confer position independent low level expression of the associated IL-2 gene, when delivered to target cells, e.g., T-cells or tumor cells, may be tested for delivery and expression of the associated gene using the above-described procedures. The transfected cells may be used to modulate the cellular immune response in cancer and AIDS where a non-physiological level of a transgene product is desired to effect such modulation.

EXAMPLE IX

Also contemplated within the invention is the combination of a chromatin opening domain with a heterologous enhancer. A heterologous COD/enhancer combination allows one of skill in the art to choose a combination which will confer a desired level of transgene expression, i.e., that is not achievable using a homologous COD/enhancer combination. The heterologous COD/enhancer combination will achieve a level of transgene expression that is either less than or better than the level of transgene expression achieved using a homologous COD/enhancer combination. As used herein, "better than" or "less than" means at least 10% or preferably 20–25% different from the level of expression of a homologous COD/enhancer combination.

Heterologous enhancers useful according to this aspect of the invention include but are not limited to the human Cytomegalovirus (CMV) enhancer, the α-globin 40 kb enhancer, SV40 enhancers, adenovirus enhancers, immunoglobulin enhancers, T cell receptor enhancers. In addition, the enhancer corresponding to the promoter and/or transgene present in the construct are useful according to the invention.

Therefore, one construct according to the invention may include the β-globin HS3 chromatin opening domain in combination with a heterologous enhancer such as the CMV enhancer or the β-globin enhancer. Thus, where the transgene is the β-globin gene, the HS3 chromatin opening domain in combination with a heterologous enhancer will allow for increased expression of the β-globin transgene in a tissue specific and position independent manner, but that level of expression will be either greater than or less than the level of expression of the transgene in combination with the complete β-globin LCR. The chromatin opening domain/heterologous enhancer combination may be tested according to procedures described herein for expression of the β-globin gene in combination with the β-globin chromatin opening domain.

EXAMPLE X

The invention also encompasses treatment of Gaucher's disease. Gaucher's disease stems from one of two different genetic mutations. Gaucher's type 1 is a CGG→CAG mutation, which results in an Arg→Gln substitution at position 119 of the β-glucocerebrosidase polypeptide (Graves, DNA 7:521, 1988). Gaucher's type 2 is a CTG→CCG mutation, which results in a Leu→Pro substitution at position 444 of the β-glucocerebrosidase polypeptide (Tsuji, NEJM 316:570, 1987). The presence of a β-glucocerebrosidase gene encoding a wild type polypeptide is believed to substantially correct Gaucher's disease.

Therefore, another construct according to the invention is one containing the chromatin opening domain of the macrophage-specific lysozyme gene LCR or the chromatin opening domain of the human lysozyme locus control region (see Bonifer et al., 1990, Euro. Mol. Biol. Org. Jour. 9;2843; and Bonifer et al., 1994, Nucleic Acids Research 22:4202–4210). These chromatin opening domains may be identified according to the procedures used, as described herein, for localization of the β-globin chromatin opening domain. That is, the macrophage-specific lysozyme chromatin opening domain will retain the tissue-specificity of the full-length lysozyme LCR, and thus will direct transgene expression primarily in macrophages, and will also retain position-independent transgene expression of the full length LCR, but will not allow for expression of the transgene to the level conferred by the full length LCR. The reduced level of transgene expression conferred by the macrophage-specific lysozyme chromatin opening domain will be less than 60% of the level of expression of the transgene when associated with the full length corresponding LCR, will likely be less than 40%, and may be on the order of 10–25%.

A construct containing the macrophage-specific lysozyme chromatin opening domain may also contain the lysozyme gene promoter and the β-glucocerebrosidase transgene (Horowitz et al., 1989, Genomics 4:87–96). This construct is made as follows.

The human β-glucocerebrosidase gene is carried, as disclosed in Horowitz et al., on a a 9722 base pair fragment extending from a BamHI site in exon 1 to an EcoRV site 3' to polyadenylation site. This fragment contains 11 exons and all intervening sequences, with translational start in exon 2. The chicken lysozyme LCR and promoter is carried on an 11.8 kb XhoI-SacI fragment from pIII.lyx construct as described in Bonifer et al., 1990 supra. This 11.8 kb fragment may be shortened to determine the location of its chromatin opening domain, as described herein, and the shortened fragment ligated to the human β-glucocerebrosidase gene.

This construct may be used to treat Gaucher's disease by introducing the construct into macrophages, as described in Immunology and Cell Biology, 1993, Vol. 71, pages 75–78 and introducing the transfected macrophages into a patient afflicted with Gaucher's disease. Expression of the wild type transgene in a patient afflicted with Gaucher's disease should result in correction of the diseased state.

EXAMPLE XI

The invention encompasses treatment of the genetic blood disorder X-linked γ-globulinemia. This disease may be treated by introducing a construct including a chromatin opening domain into pre-B cells, and subsequently introducing the genetically altered pre-B cells into a patient afflicted with the disorder.

Therefore, another construct according to the invention is one containing the chromatin opening domain of the class II major histocompatibility complex (MHC) gene LCR (Carson & Wiles, 1993, Nucleic Acids Research 21:2065–2072). The chromatin opening domain of this LCR may be identified according to the procedures used, as described herein, for localization of the β-globin LCR chromatin opening domain. That is, the class II MHC chromatin opening domain will retain the tissue-specificity of the full-length class II MHC LCR, and thus will direct transgene expression primarily in B or pre-B cells, and will also retain position-independent transgene expression of the full length LCR, but will not allow for expression of the transgene to the level conferred by the full length LCR. The reduced level of transgene expression conferred by the class II MHC chromatin opening domain will be less than 60% of the level of expression of the transgene when associated with the full length corresponding LCR, will likely be less than 40%, and may be on the order of 10–25%. The chromatin opening domain from the class II MHC will be larger than a fragment containing a deletion of three of the five DNase hypersensitive sites mapped in the MHCII LCR, as disclosed in Carson & Wiles, supra.

A construct containing the class II MHC chromatin opening domain may also contain the Bruton's kinase transgene (Vetrie et al., 1993, Nature 361:226–233). This construct may be made utilizing the following DNA fragments, which are cloned together using procedures well-known in the art. The Bruton's Tyrosine Kinase human gene is carried on a 2.1 kb fragment delineated by the PvuI site at position (+33) and the HindIII site at position (+2126). A region of the MHC II locus that has been found to confer tissue specific, position independent gene expression on the murine I-Ea gene lies in a 25 kb region of 5' flanking sequences. This 25 kb fragment is delineated by an MluI site and a PvuI site from cosmid 32.1 (see Carson & Wiles), and can be shortened and tested for chromatin opening domain activity as described herein. Finally, the construct will also encode a splice site and poly A tail, which may include portions of the human B globin locus splice and poly A signals; i.e., a BamHI-XbaI 2.8 kb 3' splice/poly A flankling sequence containing exon 2—IVSII—exon 3—polyA sequences.

The above-described construct may be used to treat X-linked γ-globulinemia by introducing the construct into pre-B cells, as described in Martensson et al., Eur. Jour. Immunol. 1987, 17:1499; Okabe et al., Eur. Jour. Immunol. 1992, 22:37; and Banerji et al., Cell 33:729, 1983, and administering the transfected pre-B cells into a patient afflicted with X-linked γ-globulinemia.

EXAMPLE XII

Another construct according to the invention is a reporter construct for testing of chromatin opening domains of the invention. This construct contains the β-galactosidase reporter gene driven by the mouse heat shock promoter 68 (hsp 68) and the β-globin HS3 COD. The construct is then used to make a transgenic mouse. A transgenic mouse containing a single copy of the reporter construct is then tested for position independent reporter gene expression. The presence of a chromatin opening domain will be indicated by position independent, copy number dependent reporter gene expression that does not rise to the level of reporter gene expression obtained using a fully functional LCR.

Other chromatin opening domains may be tested according to the invention and using the above-described reporter construct. For example, a candidate LCR is provided and subcloned. LCR subregions are then inserted into the reporter construct and tested in vivo for tissue-specific, position independent expression. Where such expression is found, a chromatin opening domain is indicated, but only if the level of transgene expression does not rise to the level of expression of the transgene when associated with the corresponding full length LCR. That is, the level of expression of a transgene when associated with a COD will be on the order of 10–25% of the level of transgene expression with the full length LCR.

OTHER EMBODIMENTS

Other embodiments will be evident to those of skill in the art. It should be understood that the foregoing detailed description is provided for clarity only and is merely exemplary. The spirit and scope of the present invention are not limited to the above examples, but are encompassed by the following claims.

We claim:

1. A method for identifying a locus control subregion (LCR) subregion comprising a chromatin opening domain, said method comprising the steps of;
   a) providing a host cell containing a DNA construct in single copy integrated into the host cell genome at a site of integration, the construct comprising a candidate LCR subregion comprising a chromatin opening domain operably linked to an expressible reporter gene, said candidate LCR subregion consisting of a single DNase I hypersensitive site; and
   b) determining that the DNA construct reproducibly actuates transcription in said host cell that is restricted to said host cell type and independent of the site of integration of said construct in the host cell genome, wherein the presence of an LCR subregion comprising a chromatin opening domain is indicated by reproducible actuation of transcription of said reporter gene in single copy in a host cell.

2. A method for identifying an LCR subregion comprising a chromatin opening domain, said method comprising the steps of;
   a) providing a host cell containing a DNA construct in single copy, the construct comprising a candidate LCR subregion comprising a chromatin opening domain operably linked to an expressible reporter gene; and
   b) determining that the DNA construct reproducibly actuates transcription in said host cell that is restricted to said host cell type and independent of the site of integration of said construct in the host cell genome; and
   c) comparing the amount of RNA encoded by said reporter gene with the amount of RNA encoded by an endogenous gene that is operably linked to an equivalent complete LCR endogenous to the host cell, wherein the presence of an LCR subregion comprising a chromatin opening domain is indicated by reproducible actuation of transcription of said reporter gene in single copy in a host cell; and wherein the presence of an LCR subregion comprising a chromatin opening domain is indicated if said reporter-gene-encoded RNA is less than about 60% of the amount of RNA encoded by said endogenous gene.

3. The method of claim 1 or claim 2, said reporter gene being the *E. coli* β-galactosidase gene.

* * * * *

UNITED STATES PATENT AND TRADEMARK OFFICE
CERTIFICATE OF CORRECTION

PATENT NO. : 6,110,666
DATED : August 29, 2000
INVENTOR(S) : Franklin G. Grosveld, James Ellis and Dimitris Kioussis It is certified that error appears in the above-identified patent and that said Letters Patent is hereby corrected as shown below:

Title page,
Item [56], References Cited, OTHER PUBLICATIONS, please delete "Dlaz et al." and insert -- Diaz et al. -- therefor.

Column 12,
Line 34, ""I" transgene" should read -- "C" transgene --.

Column 36,
Line 8, "10 A domain" should read -- A domain --.

Column 42,
Line 39, "β-globin" should read -- α-globin --.

Signed and Sealed this

Sixteenth Day of March, 2004

JON W. DUDAS
*Acting Director of the United States Patent and Trademark Office*

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: No (iv) ANTI-SENSE: No (xi) SEQUENCE DESCRIPTION: SEQ ID NO:1:

AAGCACAGCA ATGCTGAGTC ATG                                           23

(2) INFORMATION FOR SEQ ID NO:2:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: No (iv) ANTI-SENSE: No (xi) SEQUENCE DESCRIPTION: SEQ ID NO:2:

TCAATGGGGT AATCAGTGGT GTC                                           23

(2) INFORMATION FOR SEQ ID NO:3:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: No (iv) ANTI-SENSE: No (xi) SEQUENCE DESCRIPTION: SEQ ID NO:3:

GGGTGGGAGA ATCAGGAAAC TAT                                           23

(2) INFORMATION FOR SEQ ID NO:4:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: No (iv) ANTI-SENSE: No (xi) SEQUENCE DESCRIPTION: SEQ ID NO:4:

```
GTCTTAGCCA GTTCCTTACA GCT                                                      23

(2) INFORMATION FOR SEQ ID NO:5:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: No (iv) ANTI-SENSE: No (xi) SEQUENCE DESCRIPTION: SEQ ID NO:5:

TGTCACATTC TGTCTCAGGC ATC                                                      23

(2) INFORMATION FOR SEQ ID NO:6:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: No (iv) ANTI-SENSE: No (xi) SEQUENCE DESCRIPTION: SEQ ID NO:6:

TGCCAGATGT GTCTATCAGA GGT                                                      23

(2) INFORMATION FOR SEQ ID NO:7:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: No (iv) ANTI-SENSE: No (xi) SEQUENCE DESCRIPTION: SEQ ID NO:7:

CATGGTTTGA CTGTCCTGTG AGC                                                      23

(2) INFORMATION FOR SEQ ID NO:8:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: No (iv) ANTI-SENSE: No (xi) SEQUENCE DESCRIPTION: SEQ ID NO:8:

GGTGGTTGAT GGTAACACTA TGC                                                      23
```

(2) INFORMATION FOR SEQ ID NO:9:

(i) SEQUENCE CHARACTERISTICS:
        (A) LENGTH: 23 amino acids
        (B) TYPE: amino acids
        (D) TOPOLOGY: linear (ii) MOLECULE TYPE: protein (xi) SEQUENCE DESCRIPTION: SEQ ID NO:9:

```
Gly Leu Phe Gly Ala Ile Ala Gly Phe Ile Gly Ala Gly Thr Gly
 1               5                  10                  15

Gly Met Ile Ala Gly Gly Gly Cys
                20
```

(2) INFORMATION FOR SEQ ID NO:10    :

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: No (iv) ANTI-SENSE: No (xi) SEQUENCE DESCRIPTION: SEQ ID NO:10:

TCTTCAGCCT AGAGTGATGA C                                            21

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: No (iv) ANTI-SENSE: No (xi) SEQUENCE DESCRIPTION: SEQ ID NO:11:

ATAGTAGCCT TGTCCTCCTC                                              20